United States Patent
Zal et al.

(10) Patent No.: US 7,776,526 B2
(45) Date of Patent: Aug. 17, 2010

(54) **METHOD FOR THE DISSOCIATION OF THE EXTRACELLULAR HAEMOGLOBIN MOLECULE OF *ARENICOLA MARINA* AND THE CHARACTERIZATION OF THE PROTEIN CHAINS FORMING THE MOLECULE AND THE NUCLEOTIDE SEQUENCES CODING FOR SAID PROTEIN CHAINS**

(75) Inventors: Franck Zal, Morlaix-Ploujean (FR); Christine Chabasse, Nandy (FR); Morgane Rousselot, Moelan S/Mer (FR); Xavier Bailly, Cauge (FR)

(73) Assignees: Centre National de la Recherche Scientifique, Paris (FR); Universite Pierre et Marie Curie, Paris (FR)

( * ) Notice: Subject to any disclaimer, the term of this patent is extended or adjusted under 35 U.S.C. 154(b) by 972 days.

(21) Appl. No.: 10/575,628

(22) PCT Filed: Oct. 13, 2004

(86) PCT No.: PCT/FR2004/002602

§ 371 (c)(1),
(2), (4) Date: Jul. 13, 2006

(87) PCT Pub. No.: WO2005/037392

PCT Pub. Date: Apr. 28, 2005

(65) Prior Publication Data

US 2007/0037160 A1 Feb. 15, 2007

(30) Foreign Application Priority Data

Oct. 14, 2003 (FR) .................................. 03 11992

(51) Int. Cl.
*C12Q 1/68* (2006.01)
*C07K 1/00* (2006.01)
*C07H 21/04* (2006.01)

(52) U.S. Cl. ............................ 435/6; 530/350; 536/23.1

(58) Field of Classification Search ...................... 435/6; 530/350; 536/23.1
See application file for complete search history.

(56) References Cited

FOREIGN PATENT DOCUMENTS

WO     WO 01/92320     12/2001

OTHER PUBLICATIONS

Morgane Rousselot et al., "Novel dissociation mechanism of a polychaetous annelid extracellular haemoglobin", The FEBS Journal, 2006, pp. 1582-1596, vol. 273, The Authors Journal compilation.
William E. Royer, Jr., et al., "Low Resolution Crystal Structure of *Arenicola* Erythrocruorin: Influence of Coiled Coils on the Architecture of a Megadalton Respiratory Protein", Journal of Mol. Biol., 2007, pp. 228-236, vol. 365, Elsevier Ltd.
Franck Zal et al., "Quaternary structure of the extracellular haemoglobin of the lugworm *Arenicola marina*: A multi-angle-laser-light-scattering and electrospray-ionisation-mass-spectrometry analysis", Eur. J. Biochem. 1997, pp. 85-92, vol. 243.
"Molecular Shape, Dissociation, and Oxygen Binding of The Dodecamer Subunit of *Lumbricus terrestris* Hemoglobin", Angelica Krebs et al., Journal of Biological Chemistry, vol. 271, No. 31, 1996 pp. 18695-18704, XP002272714.
"The Role of the Dodecamer Subunit in the Dissociation and Reassembly of the Hexagonal Bilayer Structure of *Lumbricus terrestris* Hemoglobin," Pawan K. Sharma et al., Journal of Biological Chemistry, vol. 271, No. 15, pp. 8754-8762, XP002272715.
"The Extracellular Hemoglobin of the Earthworm, *Lumbricus terrestris*," Kenzo Fushitani et al., Journal of Biological Chemistry, vol. 266, No. 16, 1991, pp. 10275-10281, XP002272716.
"Invertebrate Oxygen Carriers," J. Sgouros et al., 1986, XP009026675.
"Quaternary Structure of the Extracellular Hemoglobin of the Lugworm *Arenicola marina*," Chemabs, XP002165190.
"Molecular Architecture of Annelid Erythrocrurins", vol. 105, pp. 131-138, XP009026718.

*Primary Examiner*—Maryam Monshipouri
(74) *Attorney, Agent, or Firm*—Young & Thompson

(57) ABSTRACT

Method of dissociating the extracellular haemoglobin molecule of annelids, e.g. *Arenicola marina*, which can be used to obtain the protein chains forming the molecule. The method includes a step of bringing an extracellular haemoglobin sample from annelids, e.g. *Arenicola marina*, into contact with at least one dissociating agent, e.g. a mixture containing dithiothreitol (DTT) or tris(2-carboxyethyl)phosphine (TCEP) hydrochloride or beta-mercaptoethanol and a dissociation buffer for a sufficient length of time in order to separate the protein chains from one another.

27 Claims, 9 Drawing Sheets

METHOD FOR THE DISSOCIATION OF THE EXTRACELLULAR HAEMOGLOBIN MOLECULE OF *ARENICOLA MARINA* AND THE CHARACTERIZATION OF THE PROTEIN CHAINS FORMING THE MOLECULE AND THE NUCLEOTIDE SEQUENCES CODING FOR SAID PROTEIN CHAINS

A subject of the present invention is a method for the dissociation of the extracellular haemoglobin molecule of Annelida, in particular of *Arenicola marina*, as well as the characterization of the protein chains constituting said molecule.

A subject of the present invention is also the characterization of the nucleotide sequences encoding the abovementioned protein chains, as well as the method for preparing these nucleotide sequences.

Blood is a complex liquid the main function of which is to transport oxygen and carbon dioxide, in order to ensure the respiratory processes. It is the haemoglobin molecule, which is found in the red blood cells, which ensures this function.

The haemoglobin molecule in mammals is formed by an assembly of four similar functional polypeptide chains in pairs (2 chains of type α globin and 2 chains of type β globin). Each of these polypeptide chains possesses the same tertiary structure of a myoglobin molecule (Dickerson and Geis, 1983).

Heme, the active site of haemoglobin, is a tetrapyrrolic protoporphyrin ring, containing a single iron atom in its centre. The iron atom, which fixes oxygen, establishes 6 coordinancy bonds: four with the nitrogen atoms of the porphyrin, one with the proximal histidine F8 and one with the oxygen molecule during the oxygenation of the globin.

We are currently faced with blood supply problems, due to the reduction in blood donations for fear of contamination. Thus, research into blood substitutes has accelerated over the last few years. We are seeking to design artificial blood substitutes capable of eliminating the risks of transmission of infectious diseases, but also to become free from problems relating to blood group compatibility.

Up to now, the main research routes relate to the synthesis of chemical products on the one hand (Clark and Gollan, 1966) and the synthesis of biological products on the other hand (Chang, 1957; Chang, 1964).

As regards the first research route, perfluorocarbons (PFCs) have been used. The PFCs are chemical products capable of transporting oxygen and they can dissolve a large quantity of gas, such as oxygen and carbon dioxide.

At present, attempts are being made to produce emulsions of these products which could be dispersed in the blood more effectively (Reiss, 1991; Reiss, 1994; Goodin et al., 1994).

The advantage of the PFCs resides in their oxyphoric capacity which is directly proportional to the quantity of oxygen to be found in the lungs. Moreover, because of the absence of a membrane to pass through, the PFCs can transport oxygen more rapidly towards the tissues. However, the long-term effects of retention of these products in the organism are not known. When these products were used for the first time in the 1960s as a blood substitute in mice (Clark and Gollan, 1966; Geyer et al., 1966; Sloviter and Kamimoto, 1967), the side effects were very significant. The PFCs were not eliminated from the circulation in a satisfactory manner and accumulated in the tissues of the organism, which caused oedema.

In the 1980s, a new version PFC was tested in the clinical phase. But the problems of storage, financial cost, non-negligible side effects and the low effectiveness of this compound prevented the extension of its marketing (Naito, 1978; Mitsuno and Naito, 1979; Mitsuno and Ohyanagi, 1985).

Recently, a new generation of PFC (PFBO perfluorooctyl-bromide) has been developed. A novel product (Reiss, 1991) is undergoing clinical trials in the United States, but it has already been noted that an increase in the quantity of oxygen in the blood can create an accumulation of oxygen in the tissues, which is dangerous to the organism (formation of superoxide-type oxygen radical).

Thus, in spite of the gradual progress made, the side effects of these compounds are still too significant for them to be marketed on a large scale.

As regards the second research route, researchers have worked on the development of blood substitutes by modifying the structure of natural haemoglobin (Chang, 1957; Chang, 1997). In order to obtain a blood substitute of modified haemoglobin type, haemoglobins synthesized by genetically modified microorganisms, or of human or animal origin are used, in particular the molecule of bovine haemoglobin. In fact, bovine haemoglobin is slightly immunologically different from human haemoglobin, but it transports oxygen towards the tissues more easily. Nevertheless, the risk of viral contamination or contamination of spongiform encephalopathy type still remain significant.

In order to be functional, the haemoglobin must be in contact with an allosteric effector, 2,3-diphosphoglycerate (2,3-DPG), present only inside the red blood cells (Dickerson and Geis, 1983). Moreover, without 2,3-DPG and other elements present in the red blood cells such as methaemoglobin reductase, haemoglobin undergoes an auto-oxidation process and loses its ability to transport oxygen or carbon dioxide.

These processes can be eliminated by modifying the structure of the haemoglobin, and more precisely by stabilizing the weak bonds of the tetrameric molecule between the two α and β dimers (Chang, 1971). Numerous modifications have been tested: covalent bond between two α chains, between two β chains or also between α and β (Payne, 1973; Bunn and Jandl, 1968).

Attempts have also been made to polymerize the tetrameric molecules or to conjugate them with a polymer named polyethylene glycol (PEG) (Nho et al., 1992). These modifications have the consequence of stabilizing the molecule and increasing its size, preventing its elimination by the kidneys.

The Annelida have been much studied for their extracellular haemoglobin (Terwilliger, 1992; Lamy et al., 1996). These extracellular haemoglobin molecules are present in the three classes of Annelida: Polychaetes, Oligochaetes and Achaetes and even in the Vestimentifera. These are giant biopolymers, made up of approximately 200 polypeptide chains belonging to 6 or 8 different types which are generally divided into two categories. The first category, comprising 144 to 192 elements, includes the so-called "functional" polypeptide chains carrying an active site and capable of reversibly binding oxygen; these are globin-type chains the masses of which are comprised between 15 and 18 kDa and which are very similar to the α and β type chains of vertebrates. The second category, comprising 36 to 42 elements, includes the so-called "structural" polypeptide chains possessing few or no active sites but allowing the assembly of "twelfths".

The first images of extracellular haemoglobins of *Arenicola* obtained (Roche et al., 1960) revealed hexagonal structures. Each haemoglobin molecule is made up of two superimposed hexagons (Levin, 1963; Roche, 1965) described as a "hexagonal bilayer" and each hexagon is itself formed by the assembly of six elements in the form of a drop of water (Van Bruggen and Weber, 1974; Kapp and Crewe, 1984), described as a "hollow globular structure" (De Haas et al., 1996) or "twelfth". The native molecule is formed of twelve of these sub-units, with a molecular mass of approximately 250 kDa.

Thus, the French patent no. 2 809 624 relates to the use as a blood substitute of extracellular haemoglobin of *Arenicola marina*, a Polychaete Annelida of the intertidal ecosystem, said blood substitute making it possible to eliminate the problems of a shortage of donations.

Although the overall architecture of the haemoglobin of *Arenicola marina* is known, in particular thanks to its fine quaternary study by mass spectrometry (Zal et al., 1997), the primary sequences of the different protein chains which compose it are not.

Thus, the purpose of the present invention is to provide the protein sequences which compose the haemoglobin molecule of *Arenicola marina*.

Another purpose of the present invention is to provide the first stages of in vitro synthesis of extracellular haemoglobin of *Arenicola marina* in order to develop a blood substitute by means of biochemistry and molecular biology methods.

Another purpose of the present invention is to provide a method for preparing the haemoglobin molecule, optionally simplified, by genetic engineering, in order in particular to increase the stock of this molecule within the framework of use as a blood substitute.

The present invention relates to a method for the dissociation of the extracellular haemoglobin molecule of Annelida, in particular of *Arenicola marina*, making it possible to obtain protein chains constituting said molecule, said method being characterized in that it comprises a stage of bringing together a sample of extracellular haemoglobin of Annelida, in particular of *Arenicola marina* and at least one dissociating agent, in particular a mixture made up of dithiothreitol (DTT) or tris(2-carboxyethyl)phosphine hydrochloride (TCEP) or beta-mercaptoethanol and a dissociation buffer, for a sufficient time to separate the protein chains from each other.

The present invention relates to a method for obtaining protein chains constituting the extracellular haemoglobin molecule of Annelida, in particular of *Arenicola marina*, said method being characterized in that it comprises a stage of bringing together a sample of extracellular haemoglobin of Annelida, in particular of *Arenicola marina* and at least one dissociating agent, and if appropriate a reducing agent, in particular a mixture made up of dithiothreitol (DTT) or tris (2-carboxyethyl)phosphine hydrochloride (TCEP) or beta-mercaptoethanol and a dissociation buffer, for a sufficient time to separate the protein chains from each other.

The term "extracellular haemoglobin" designates a haemoglobin not contained in the cells and dissolved in the blood.

The expression "dissociation" designates a chemical treatment capable of breaking weak interactions (hydrophobic, electrostatic, hydrogen etc.).

The term "dissociation buffer" designates a liquid containing a buffer making it possible to adjust the pH and containing dissociating agents.

The expression "dissociating agent" designates a chemical compound capable of breaking weak interactions (hydrophobic, electrostatic, hydrogen etc.). Said dissociating agent is in particular chosen from: hydroxide ions, urea or heteropolytungstate ions or guanidinium salts or SDS (sodium dodecyl sulphate).

The expression "reduction" designates a chemical treatment capable of breaking strong interactions such as disulphide bridges.

The expression "reducing agent" designates a chemical compound capable of breaking strong interactions such as disulphide bridges.

The ten protein chains constituting the extracellular haemoglobin molecule of *Arenicola marina* include 8 globin-type chains and 2 structural-type chains.

It is recalled that the extracellular haemoglobin of *Arenicola marina* with a mass of 3648±24 kDa is made up of 198 polypeptide chains belonging to 10 different types divided into two categories:

the first (156 chains) includes so-called "functional" polypeptide chains carrying an active site capable of reversibly binding oxygen; these are globin-type chains the masses of which are comprised between 15 and 18 kDa; these chains are very similar to the $\alpha$ and $\beta$-type chains of vertebrates; and the second (42 chains) includes so-called "structural" (or "linker") polypeptide chains possessing few or no active sites but allowing the assembly of the dodecamers; these chains have molecular masses comprised between 22 and 27 kDa.

The present invention relates to a method for the dissociation of the extracellular haemoglobin molecule of *Arenicola marina*, making it possible to obtain protein chains constituting said molecule, said method being characterized in that it comprises a stage of bringing together a sample of extracellular haemoglobin of *Arenicola marina* and a mixture made up of dithiothreitol (DTT) and a dissociation buffer, for approximately one hour to three weeks.

An advantageous dissociation method of the invention is characterized in that the dissociation buffer comprises a buffering agent at a concentration comprised between approximately 0.05 M and approximately 0.1 M, in particular Trisma (tris[hydroxymethyl]aminomethane), hepes, sodium phosphate, sodium borate, ammonium bicarbonate or ammonium acetate, and 0 to 10 mM of EDTA adjusted to a pH comprised between approximately 5 and approximately 12, and preferably between approximately 7.5 and 12, the whole being in particular adjusted to a pH comprised between approximately 2 and 12, and preferably between approximately 5 and 12.

Preferably, said dissociation buffer comprises EDTA at a concentration of approximately 1 mM adjusted to a pH of approximately 10, in particular with a 2N solution of soda.

According to an advantageous embodiment, the method of the invention is characterized in that the protein chains constituting said molecule are obtained by the reduction of four sub-units by a reducing agent, for example in the presence of DTT, said sub-units themselves being obtained by bringing together a sample of extracellular haemoglobin of *Arenicola marina* and different dissociating agents, in particular a dissociation buffer.

The native molecule is dissociated into sub-units under the action of non-reducing dissociating agents. There is therefore no breakage of the covalent bonds. However, after the action of a reducing agent (cleavage of the covalent bonds), the sub-units are reduced to polypeptide chains (protein chains made up of the assembly of amino acids).

The abovementioned 4 sub-units are therefore: monomers, dimers, trimers and dodecamers.

The monomers are globin chains.

The dimers in the homo form and heterodimers are structural chains.

The trimers are covalent assemblies of three globin chains.

The dodecamers are made up of 12 protein chains; for example: 3 trimers+3 monomers, 2 trimers+6 monomers, 1 trimer+9 monomers.

It is therefore possible to obtain the protein chains either in a single stage by direct reduction of the extracellular haemoglobin of *Arenicola marina*, or in two stages, one consisting of the dissociation of the extracellular haemoglobin of *Arenicola marina* into 4 sub-units and the other being the reduction of said 4 sub-units into protein chains.

The present invention also relates to a dissociation method as defined above, characterized in that the dissociating agents used in order to obtain the abovementioned 4 sub-units are the following:
- a dissociation buffer solution comprising: 0.1 M of Trisma base (tris[hydroxymethyl]aminomethane) and 0 to 10 mM of EDTA adjusted to a pH comprised between approximately 5 and approximately 12, and preferably between approximately 7.5 and approximately 12, and
- a urea solution, the concentration of which is comprised between approximately 0.1 M and approximately 8 M, and is in particular equal to 3 M.

The present invention also relates to a dissociation method as defined above, characterized in that the dissociating agents for obtaining the 4 sub-units are the following:
- a dissociation buffer solution comprising 0.1 M of Trisma base and 1 mM of EDTA adjusted to pH 10, and
- 3 M of urea.

The present invention also relates to a dissociation and reduction method as defined above, characterized in that the dissociating and reducing agents used in order to obtain the protein chains are the following:
- a dissociation buffer solution comprising: 0.1 M of Trisma base (tris[hydroxymethyl]aminomethane) at a pH comprised between approximately 8 and approximately 9, and
- a urea solution, the concentration of which is comprised between approximately 4 M and approximately 8 M, and is in particular equal to 8 M, and
- 1 to 10% DTT or
- a dissociation buffer solution comprising: 0.1 M of ammonium bicarbonate at a pH comprised between approximately 8 and approximately 9, and
- 1 to 10% DTT The dissociation and reduction method of the invention makes it possible to obtain a composition containing the mixture of the protein chains constituting the extracellular haemoglobin molecule of *Arenicola marina*.

The present invention also relates to a method for preparing primer pairs from the protein chains as obtained according to the method as defined above, said method being characterized in that it comprises the following stages:
- the isolation of each of the protein chains constituting the haemoglobin molecule as obtained according to the method as defined above,
- the microsequencing of each of the abovementioned isolated protein chains by mass spectrometry and Edman sequencing, in order to obtain a microsequence corresponding to each of the sequences made up of 5 to 20 amino acids, and
- the determination of the degenerated primers from the abovementioned microsequences.

The first stage of isolation of the protein chains is in particular carried out by Reversed-phase liquid chromatography and two-dimensional gel from the abovementioned mixture comprising the protein chains constituting the haemoglobin molecule as obtained according to the dissociation and reduction method of the invention.

The expression "microsequence" designates fragments of protein sequences.

The abovementioned microsequences can originate both from the C- and N-terminal ends but also from internal sequences.

The protein chains can be obtained by Reversed-phase liquid chromatography or from 2D gel from purified haemoglobin of *Arenicola marina*. Each peak or spot was cut out and digested by a protease. The peptides thus obtained were extracted from the gels and separated by capLC (capillary liquid chromatography). The fragments are then analyzed by mass spectrometry. On the other hand, each peak isolated by Reversed-phase was analyzed by Edman sequencing.

The expression "degenerated primers" designates nucleotide sequences obtained from fragments of protein sequences. They are called degenerated primers because of the degeneration of the genetic code (several codons for 1 amino acid).

The last stage of determination of the degenerated primer pairs corresponds to their synthesis.

This stage makes it possible to obtain both sense primers and antisense primers.

The present invention also relates to primer pairs as obtained according to the method as defined above, said pairs being in particular the following:

a) Sense primer:     GAR TGY GGN    (SEQ ID NO: 21)
                     CCN TTR CAR
                     CG Antisense primer: CTC CTC TCC    (SEQ ID NO: 22)
                     TCT CCT CTT
                     CCT b) Sense primer:     TGY GGN ATH    (SEQ ID NO: 23)
                     CTN CAR CG Antisense primer: CTC CTC TCC    (SEQ ID NO: 22)
                     TCT CCT CTT
                     CCT c) Sense primer:     AAR GTI AAR    (SEQ ID NO: 24)
                     CAN AAC TGG Antisense primer: CTC CTC TCC    (SEQ ID NO: 22)
                     TCT CCT CTT
                     CCT d) Sense primer:     TGY TGY AGY    (SEQ ID NO: 25)
                     ATH GAR GAY
                     CG Antisense primer: CTC CTC TCC    (SEQ ID NO: 22)
                     TCT CCT CTT
                     CCT e) Sense primer:     AAR GTN ATH    (SEQ ID NO: 26)
                     TTY GGN AGR
                     GA Antisense primer: CTC CTC TCC    (SEQ ID NO: 22)
                     TCT CCT CTT
                     CCT f) Sense primer:     GAR CAY CAR    (SEQ ID NO: 27)
                     TGY GGN GGN
                     GA Antisense primer: CTC CTC TCC    (SEQ ID NO: 22)
                     TCT CCT CTT
                     CCT where:
R represents A or G,
Y represents C or T,
N represents A, G, C or T,
I represents inosine,
H represents A, C or T.

The present invention also relates to primer pairs as obtained according to the method as defined above, said pairs being in particular the following:

```
a) Sense primer:      GAR TGY GGN       SEQ ID NO: 21
                      CCN TTR CAR
                      CG Antisense primer:  CCA NGC NTC       SEQ ID NO: 28
                      YTT RTC RAA
                      GCA b) Sense primer:      AN TGY GGN        SEQ ID NO: 29
                      CCN CTN CAR
                      CG Antisense primer:  CCA NGC NTC       SEQ ID NO: 28
                      YTT RTC RAA
                      GCA c) Sense primer:      AAR GTI AAR       SEQ ID NO: 24
                      CAN AAC TGG Antisense primer:  CCA NGC NCC       SEQ ID NO: 30
                      DAT RTC RAA d) Sense primer:      TGY TGY AGY       SEQ ID NO: 25
                      ATH GAR GAY
                      CG Antisense primer:  CA NGC NYC        SEQ ID NO: 31
                      RCT RTT RAA
                      RCA
``` where:
R represents A or G,
Y represents C or T,
N represents A, G, C or T,
I represents inosine,
D represents A, G or T,
H represents A, C or T.

The present invention also relates to a method for preparing nucleotide sequences encoding the protein chains constituting the haemoglobin molecule of *Arenicola marina*, from the primers as obtained according to the method as defined above, said method being characterized in that it corresponds to a polymerase chain amplification method (PCR), comprising a repetition of at least 30 times the cycle constituted by the following stages:

the denaturation, by heating, of the monocatenary cDNA encoding one of the protein chains constituting the haemoglobin molecule of *Arenicola marina*, so as to denature any secondary structures and RNA residuals, said cDNA being obtained from mRNA, this stage making it possible to obtain strands of denatured monocatenary cDNA, the hybridization of the primer pairs as obtained by the method as defined above to the strands of abovementioned denatured monocatenary cDNA at an appropriate temperature, in order to obtain hybridized primers, and the synthesis of the complementary strand of the cDNA by a polymerase at an appropriate temperature, from the hybridized primers as obtained in the preceding stage.

The cDNA encoding the abovementioned protein chains is obtained from mRNA, said mRNA being obtained by purification from total RNAs extracted from growing juvenile Arenicolae, said juvenile Arenicolae having a high level of transcription of the different messenger RNAs.

If the abovementioned cycle is repeated less than 30 times, the amplification of the DNA is reduced.

The expression "optional secondary structures" designates anarchic pairings between two sequences of cDNA.

The expression "denaturation by heating of the cDNA" designates the breaking of the anarchic pairings between two sequences of cDNA.

The expression "hybridization at an appropriate temperature" designates the recognition by the primers of their complementary sequences on the DNA matrix.

According to an advantageous embodiment, the method for preparing nucleotide sequences according to the invention is characterized in that:

the first stage of said method is a stage of denaturation of the cDNA encoding one of the protein chains constituting the haemoglobin molecule of *Arenicola marina* of approximately 10 seconds to approximately 5 minutes at a temperature comprised between approximately 90° C. and approximately 110° C., the cycle, repeated approximately 30 to 40 times, comprises the following stages:

a stage of denaturation of the cDNA encoding one of the protein chains constituting the haemoglobin molecule of *Arenicola marina* of approximately 10 seconds to approximately 5 minutes, at a temperature comprised between approximately 90° C. and approximately 110° C., a stage of hybridization of the primer pairs of the invention to the abovementioned strands of monocatenary cDNA in order to obtain hybridized primers, of approximately 20 seconds to approximately 2 minutes, at a temperature comprised between approximately 50° C. and approximately 60° C., preferably between approximately 50° C. and approximately 56° C., a stage of elongation of the hybridized primers as obtained previously by a polymerase of approximately 20 seconds to approximately 1 minute and 30 seconds, at a temperature comprised between approximately 70° C. and approximately 75° C., and the last stage of the method is a stage of elongation of the hybridized primers as obtained previously by a polymerase of approximately 5 minutes to approximately 15 minutes at a temperature comprised between approximately 70° C. and approximately 75° C.

The PCR reaction of the method of the invention is in particular carried out in the presence of cDNA (5 to 20 ng), sense (100 ng) and antisense (100 ng) primer, dNTP (200 µM final), MgCl$_2$ (2 mM final), PCR buffer (supplied with the polymerase) (1× final), Taq polymerase (1 unit) and water (25 µl qsf).

The method for preparing the abovementioned nucleotide sequences makes it possible to obtain partial coding sequences.

Once the partial coding sequences have been obtained by means of the preceding experiments, the amplification and the sequencing of the whole of the coding sequence of the cDNA of globins and of the linker are carried out by 5' RACE Rapid Amplification cDNA Ends) PCR and according to the protocol recommendations of the data sheet provided by the supplier (5'/3' RACE kit, Roche).

The present invention also relates to a preparation method as defined above, characterized in that the primer pairs used are as defined previously.

A particularly advantageous preparation method according to the invention is a method for preparing nucleotide sequences as defined above, characterized in that the pair of primers used is: (GAR TGY GGN CCN TTR CAR CG (SEQ ID NO: 21); CCA NGC NTC YTT RTC RAA GCA (SEQ ID NO: 28)) or (GAR TGY GGN CCN TTR CAR CG (SEQ ID NO: 21); CTC CTC TCC TCT CCT CTT CCT (SEQ ID NO: 22)), R, Y and N being as defined above, said method being characterized in that:
the first stage of the method is a stage of denaturation of the cDNA encoding the protein chains constituting the haemoglobin molecule of *Arenicola marina*, of 4 minutes at a temperature equal to 95° C.,
the cycle, repeated 35 times, comprises the following stages:
a stage of denaturation of the cDNA encoding one of the protein chains constituting the haemoglobin molecule of *Arenicola marina*, of 30 seconds at a temperature equal to 95° C.,
a stage of hybridization of the primer pairs of the invention to the abovementioned strands of monocatenary cDNA in order to obtain hybridized primers, of 30 seconds at a temperature equal to 56° C.,
a stage of elongation of the hybridized primers as obtained previously by a polymerase of 40 seconds at a temperature equal to 72° C., and
the last stage of the method is a stage of elongation of the hybridized primers as obtained previously by a polymerase of 10 minutes at a temperature equal to 72° C.,
in order to obtain the nucleotide sequence SEQ ID NO: 13,
said method optionally comprising an additional stage of 5' RACE PCR in order to obtain the nucleotide sequence SEQ ID NO: 1.

The partial sequence SEQ ID NO: 13 was then completed by 5' RACE PCR experiments as explained above. The nucleotide sequence SEQ ID NO: 13 is a novel nucleotide sequence encoding a protein chain corresponding to a globin chain, denoted A2a. SEQ ID NO: 13 comprises 376 nucleotides.

The nucleotide sequence SEQ ID NO: 1 (from the start codon to the stop codon, i.e. the transcribed and translated sequence which corresponds to a functional globin monomer) is a novel nucleotide sequence encoding a protein chain corresponding to the abovementioned globin chain, denoted A2a. SEQ ID NO: 1 comprises 474 nucleotides.

A particularly advantageous preparation method according to the invention is a method for preparing nucleotide sequences as defined above, characterized in that the pair of primers used is the following: (AN TGY GGN CCN CTN CAR CG (SEQ ID NO: 29); CCA NGC NTC YTT RTC RAA GCA (SEQ ID NO: 28)), N, Y and R being as defined above,
said method being characterized in that:
the first stage of the method is a stage of denaturation of the cDNA encoding the protein chains constituting the haemoglobin molecule of *Arenicola marina*, of 4 minutes at a temperature equal to 95° C.,
the cycle, repeated 35 times, comprises the following stages:
a stage of denaturation of the cDNA encoding one of the protein chains constituting the haemoglobin molecule of *Arenicola marina*, of 30 seconds at a temperature equal to 95° C.,
a stage of hybridization of the primer pairs of the invention to the abovementioned strands of monocatenary cDNA in order to obtain hybridized primers, of 30 seconds at a temperature equal to 52° C.,
a stage of elongation of the hybridized primers as obtained previously by a polymerase of 40 seconds at a temperature equal to 72° C., and
the last stage of the method is a stage of elongation of the hybridized primers as obtained previously by a polymerase of 10 minutes at a temperature equal to 72° C.,
in order to obtain the nucleotide sequence SEQ ID NO: 15.

The nucleotide sequence SEQ ID NO: 15 is a novel nucleotide sequence encoding a protein chain corresponding to a globin chain, denoted A2b. SEQ ID NO: 15 comprises 288 nucleotides.

A particularly advantageous preparation method according to the invention is a method for preparing nucleotide sequences as defined above, characterized in that the pair of primers used is the following: (TGY GGN ATH CTN CAR CG (SEQ ID NO: 23); CTC CTC TCC TCT CCT CTT CCT (SEQ ID NO: 22)), N, Y and R being as defined above, said method being characterized in that:
the first stage of the method is a stage of denaturation of 4 minutes at a temperature equal to 95° C.,
the cycle, repeated 35 times, comprises the following stages:
a stage of denaturation of 30 seconds at a temperature equal to 95° C.,
a stage of hybridization of 30 seconds at a temperature equal to 53° C.,
a stage of elongation of 40 seconds at a temperature equal to 72° C., and
the last stage of the method is a stage of elongation of 10 minutes at a temperature equal to 72° C.,
in order to obtain the nucleotide sequence SEQ ID NO: 15,
said method optionally comprising an additional stage of 5' RACE PCR in order to obtain the nucleotide sequence SEQ ID NO: 3.

The partial sequence SEQ ID NO: 15 was then completed by 5' RACE PCR experiments as explained above.

The nucleotide sequence SEQ ID NO: 3 (from the start codon to the stop codon, i.e. the transcribed and translated sequence which corresponds to a functional globin monomer) is a novel nucleotide sequence encoding a protein chain corresponding to the abovementioned globin chain, denoted A2b. SEQ ID NO: 3 comprises 477 nucleotides.

A particularly advantageous preparation method according to the invention is a method for preparing nucleotide sequences as defined above, characterized in that the pair of primers used is: (AAR GTI AAR CAN AAC TGG (SEQ ID NO: 24); CCA NGC NCC DAT RTC RAA (SEQ ID NO: 30)) or (AAR GTI AAR CAN AAC TGG (SEQ ID NO: 24); CTC CTC TCC TCT CCT CTT CCT (SEQ ID NO: 22)), R, I, N and D being as defined above, said method being characterized in that:
the first stage of the method is a stage of denaturation of the cDNA encoding each of the protein chains constituting the haemoglobin molecule of *Arenicola marina*, of 4 minutes at a temperature equal to 95° C.,
the cycle, repeated 35 times, comprises the following stages:
a stage of denaturation of the cDNA encoding one of the protein chains constituting the haemoglobin molecule of *Arenicola marina*, of 1 minute at a temperature equal to 95° C.,
a stage of hybridization of the primer pairs of the invention to the abovementioned strands of monocatenary cDNA in order to obtain hybridized primers, of 1 minute at a temperature equal to 50° C.,
a stage of elongation of the hybridized primers as obtained previously by a polymerase of 1 minute and 30 seconds at a temperature equal to 72° C., and
the last stage of the method is a stage of elongation of the hybridized primers as obtained previously by a polymerase of 10 minutes at a temperature equal to 72° C.,
in order to obtain the nucleotide sequence SEQ ID NO: 17, said method optionally comprising an additional stage of 5' RACE PCR in order to obtain the nucleotide sequence SEQ ID NO: 5.

The partial sequence SEQ ID NO: 17 was then completed by 5' RACE PCR experiments as explained above. The nucleotide sequence SEQ ID NO: 17 is a novel nucleotide sequence encoding a protein chain corresponding to a globin chain, denoted A1. SEQ ID NO: 17 comprises 360 nucleotides.

The nucleotide sequence SEQ ID NO: 5 (from the start codon to the stop codon, i.e. the transcribed and translated sequence which corresponds to a functional globin monomer) is a novel nucleotide sequence encoding a protein chain corresponding to the abovementioned globin chain, denoted A1. SEQ ID NO: 5 comprises 474 nucleotides.

A particularly advantageous preparation method according to the invention is a method for preparing nucleotide sequences as defined above, characterized in that the pair of primers used is the following: (TGY TGY AGY ATH GAR GAY CG (SEQ ID NO: 25); CA NGC NYC RCT RTT RAA RCA (SEQ ID NO: 31)) or (TGY TGY AGY ATH GAR GAY CG (SEQ ID NO: 25); CTC CTC TCC TCT CCT CTT CCT (SEQ ID NO: 22)), Y, H, R and N being as defined above, said method being characterized in that:
the first stage of the method is a stage of denaturation of the cDNA encoding each of the protein chains constituting the haemoglobin molecule of *Arenicola marina*, of 4 minutes at a temperature equal to 95° C.,
the cycle, repeated 35 times, comprises the following stages:
a stage of denaturation of the cDNA encoding one of the protein chains constituting the haemoglobin molecule of *Arenicola marina*, of 30 seconds at a temperature equal to 95° C.,
a stage of hybridization of the primer pairs of the invention to the abovementioned strands of monocatenary cDNA in order to obtain hybridized primers, of 40 seconds at a temperature equal to 52° C.,
a stage of elongation of the hybridized primers as obtained previously by a polymerase of 30 seconds at a temperature equal to 72° C., and
the last stage of the method is a stage of elongation of the hybridized primers as obtained previously by a polymerase of 10 minutes at a temperature equal to 72° C.,
in order to obtain the nucleotide sequence SEQ ID NO: 19,
said method optionally comprising an additional stage of 5' RACE PCR in order to obtain the nucleotide sequence SEQ ID NO: 7.

The partial sequence SEQ ID NO: 19 was then completed by 5' RACE PCR experiments as explained above. The nucleotide sequence SEQ ID NO: 19 is a novel nucleotide sequence encoding a protein chain corresponding to a globin chain, denoted B2. SEQ ID NO: 19 comprises 390 nucleotides.

The nucleotide sequence SEQ ID NO: 7 (from the start codon to the stop codon, i.e. the transcribed and translated sequence which corresponds to a functional globin monomer) is a novel nucleotide sequence encoding a protein chain corresponding to the abovementioned globin chain, denoted B2. SEQ ID NO: 7 comprises 498 nucleotides.

A particularly advantageous preparation method according to the invention is a method for preparing nucleotide sequences as defined above, characterized in that the pair of primers used is the following: (AAR GTN ATH TTY GGN AGR GA (SEQ ID NO: 26); CTC CTC TCC TCT CCT CTT CCT (SEQ ID NO: 22)), R, H, N and Y being as defined above,
said method being characterized in that:

the first stage of the method is a stage of denaturation of 4 minutes at a temperature equal to 95° C.,
the cycle, repeated 35 times, comprises the following stages:
a stage of denaturation of 30 seconds at a temperature equal to 95° C.,
a stage of hybridization of 40 seconds at a temperature equal to 52° C.,
a stage of elongation of 30 seconds at a temperature equal to 72° C., and
the last stage of the method is a stage of elongation of 10 minutes at a temperature equal to 72° C.,
in order to obtain a reference partial nucleotide sequence in order to continue the complete determination of this coding sequence,
said method comprising an additional stage of 5' RACE PCR in order to obtain the nucleotide sequence SEQ ID NO: 9.

The nucleotide sequence SEQ ID NO: 9 (from the start codon to the stop codon, i.e. the transcribed and translated sequence which corresponds to a functional globin monomer) is a novel nucleotide sequence encoding a protein chain corresponding to a globin chain, denoted B1. SEQ ID NO: 9 comprises 498 nucleotides.

A particularly advantageous preparation method according to the invention is a method for preparing nucleotide sequences as defined above, characterized in that the pair of primers used is the following: (GAR CAY CAR TGY GGN GGN GA (SEQ ID NO: 27), CTC CTC TCC TCT CCT CTT CCT (SEQ ID NO: 22)), R, N and Y being as defined above,
said method being characterized in that:
the first stage of the method is a stage of denaturation of 4 minutes at a temperature equal to 95° C.,
the cycle, repeated 35 times, comprises the following stages:
a stage of denaturation of 40 seconds at a temperature equal to 95° C.,
a stage of hybridization of 1 minute at a temperature equal to 58° C.,
a stage of elongation of 1 minute and 10 seconds at a temperature equal to 72° C., and
the last stage of the method is a stage of elongation of 10 minutes at a temperature equal to 72° C.,
in order to obtain a reference partial nucleotide sequence in order to continue the complete determination of this coding sequence,
said method comprising an additional stage of 5' RACE PCR in order to obtain the nucleotide sequence SEQ ID NO: 11.

The nucleotide sequence SEQ ID NO: 11 (from the start codon to the stop codon, i.e. the transcribed and translated sequence which corresponds to a functional globin monomer) is a novel nucleotide sequence encoding a protein chain corresponding to a linker chain, denoted L1. SEQ ID NO: 11 comprises 771 nucleotides.

The present invention also relates to protein sequences encoded by one of the nucleotide sequences as obtained according to the method as defined above.

A preferred protein according to the invention is a protein as defined above, characterized in that it comprises or is constituted by:
the sequence SEQ ID NO: 2 or SEQ ID NO: 14,
or any sequence derived from the sequence SEQ ID NO: 2 or SEQ ID NO: 14 or from a fragment defined below, in particular by substitution, suppression or addition of one or more amino acids, provided that said derived sequence allows the transport of oxygen, or any sequence homologous to the sequence SEQ ID NO: 2 or SEQ ID NO: 14 or to a fragment defined below, preferably having a homology of at least approximately 75%, in particular of at least approximately 85%, with the sequence SEQ ID NO: 2 or SEQ ID NO: 14, provided that said homologous sequence allows the transport of oxygen, or any fragment of one of the sequences defined above, provided that said fragment allows the transport of oxygen, in particular any fragment being made up of at least approximately 60 amino acids, and in particular at least approximately 160 contiguous amino acids in the sequence SEQ ID NO: 2.

The sequence SEQ ID NO: 2 is a novel protein sequence corresponding to a whole globin chain, denoted A2a.

The sequence SEQ ID NO: 14 is a novel protein sequence corresponding to a fragment of a sequence derived from the globin chain, denoted A2a, represented by the sequence SEQ ID NO: 2.

The oxygen transport properties of the protein sequences of the invention can be in particular verified by measuring their absorption spectrum by typical oxyhaemoglobin spectrophotometry.

A preferred protein according to the invention is a protein as defined above, characterized in that it comprises or is constituted by:

the sequence SEQ ID NO: 4 or SEQ ID NO: 16, or any sequence derived from the sequence SEQ ID NO: 4 or SEQ ID NO: 16, or from a fragment defined below, in particular by substitution, suppression or addition of one or more amino acids, provided that said derived sequence allows the transport of oxygen, or any sequence homologous to the sequence SEQ ID NO: 4 or SEQ ID NO: 16, or to a fragment defined below, preferably having a homology of at least approximately 75%, in particular of at least approximately 85%, with the sequence SEQ ID NO: 4 or SEQ ID NO: 16, provided that said homologous sequence allows the transport of oxygen, or any fragment of one of the sequences defined above, provided that said fragment allows the transport of oxygen, in particular any fragment being made up of at least approximately 60 amino acids, and in particular of at least approximately 160 contiguous amino acids in the sequence SEQ ID NO: 4.

The sequence SEQ ID NO: 4 is a novel protein sequence corresponding to a whole globin chain, denoted A2b.

The sequence SEQ ID NO: 16 is a novel protein sequence corresponding to a fragment of a sequence derived from the globin chain, denoted A2b, represented by the sequence SEQ ID NO: 4.

A preferred protein according to the invention is a protein as defined above, characterized in that it comprises or is constituted by:

the sequence SEQ ID NO: 6 or SEQ ID NO: 18, or any sequence derived from the sequence SEQ ID NO: 6 or SEQ ID NO: 18 or from a fragment defined below, in particular by substitution, suppression or addition of one or more amino acids, provided that said derived sequence allows the transport of oxygen, or any sequence homologous to the sequence SEQ ID NO: 6 or SEQ ID NO: 18 or to a fragment defined below, preferably having a homology of at least approximately 75%, in particular of at least approximately 85%, with the sequence SEQ ID NO: 6 or SEQ ID NO: 18, provided that said homologous sequence allows the transport of oxygen, or any fragment of one of the sequences defined above, provided that said fragment allows the transport of oxygen, in particular any fragment being made up of at least approximately 60 amino acids, and in particular of at least approximately 160 contiguous amino acids in the sequence SEQ ID NO: 6.

The sequence SEQ ID NO: 6 is a novel protein sequence corresponding to an entire globin chain, denoted A1.

The sequence SEQ ID NO: 18 is a novel protein sequence corresponding to a fragment of a sequence derived from the globin chain, denoted A1, represented by the sequence SEQ ID NO: 6.

A preferred protein according to the invention is a protein as defined above, characterized in that it comprises or is constituted by:

the sequence SEQ ID NO: 8 or SEQ ID NO: 20, or any sequence derived from the sequence SEQ ID NO: 8 or SEQ ID NO: 20 or from a fragment defined below, in particular by substitution, suppression or addition of one or more amino acids, provided that said derived sequence allows the transport of oxygen, or any sequence homologous to the sequence SEQ ID NO: 8 or SEQ ID NO: 20 or to a fragment defined below, preferably having a homology of at least approximately 75%, in particular of at least approximately 85%, with the sequence SEQ ID NO: 8 or SEQ ID NO: 20, provided that said homologous sequence allows the transport of oxygen, or any fragment of one of the sequences defined above, provided that said fragment allows the transport of oxygen, in particular any fragment being made up of at least approximately 60 amino acids, and in particular of at least approximately 160 contiguous amino acids in the sequence SEQ ID NO: 8.

The sequence SEQ ID NO: 8 is a novel protein sequence corresponding to a whole globin chain, denoted B2.

The sequence SEQ ID NO: 20 is a novel protein sequence corresponding to a fragment of a sequence derived from the globin chain, denoted B2, represented by the sequence SEQ ID NO: 8.

A preferred protein according to the invention is a protein as defined above, characterized in that it comprises or is constituted by:

the sequence SEQ ID NO: 10, or any sequence derived from the sequence SEQ ID NO: 10 or from a fragment defined below, in particular by substitution, suppression or addition of one or more amino acids, provided that said derived sequence allows the transport of oxygen, or any sequence homologous to the sequence SEQ ID NO: 10 or to a fragment defined below, preferably having a homology of at least approximately 75%, with the sequence SEQ ID NO: 10, provided that said homologous sequence allows the transport of oxygen, or any fragment of one of the sequences defined above, provided that said fragment allows the transport of oxygen, in particular any fragment being made up of at least approximately 60 amino acids, and in particular of at least approximately 160 contiguous amino acids in the sequence SEQ ID NO: 10.

The sequence SEQ ID NO: 10 is a novel protein sequence corresponding to a globin chain, denoted B1.

A preferred protein according to the invention is a protein as defined above, characterized in that it comprises or is constituted by:

the sequence SEQ ID NO: 12, or any sequence derived from the sequence SEQ ID NO: 12 or from a fragment defined below, in particular by substitution, suppression or addition of one or more amino acids, provided that said derived sequence allows the combination of globin chains with each other, or any sequence homologous to the sequence SEQ ID NO: 12 or to a fragment defined below, preferably having a homology of at least approximately 75%, with the sequence SEQ ID NO: 12, provided that said homologous sequence allows the combination of globin chains with each other, or any fragment of one of the sequences defined above, provided that said fragment allows the combination of globin chains with each other, in particular any fragment being made up of at least approximately 60 amino acids, and in particular of at least approximately 280 contiguous amino acids in the sequence SEQ ID NO: 12.

The sequence SEQ ID NO: 12 is a novel protein sequence corresponding to a linker chain, denoted L1.

The present invention also relates to nucleotide sequences as obtained according to the method as defined above.

The present invention also relates to nucleotide sequences encoding a protein as defined above.

The present invention also relates to a nucleotide sequence as defined above, characterized in that it comprises or is constituted by:

the nucleotide sequence SEQ ID NO: 1 or SEQ ID NO: 13 encoding SEQ ID NO: 2 or SEQ ID NO: 14 respectively, or any nucleotide sequence derived, by degeneration of the genetic code, from the sequence SEQ ID NO: 1 or SEQ ID NO: 13, and encoding a protein represented by SEQ ID NO: 2 or SEQ ID NO: 14 respectively, or any nucleotide sequence derived, in particular by substitution, suppression or addition of one or more nucleotides, from the sequence SEQ ID NO: 1 or SEQ ID NO: 13 encoding a protein derived from SEQ ID NO: 2 or SEQ ID NO: 14 respectively, or any nucleotide sequence homologous to SEQ ID NO: 1 or SEQ ID NO: 13, preferably having a homology of at least approximately 60%, with the sequence SEQ ID NO: 1, or any fragment of the nucleotide sequence SEQ ID NO: 1 or of the nucleotide sequences defined above, said fragment preferably being made up of at least approximately 180 nucleotides, and in particular of at least approximately 480 contiguous nucleotides in said sequence, or any nucleotide sequence complementary to the abovementioned sequences or fragments, or any nucleotide sequence capable of hybridizing under stringent conditions with the sequence complementary to one of the abovementioned sequences or fragments.

The stringency conditions correspond to temperature ranges comprised between 48 and 60° C. and MgCl$_2$ concentrations comprised between 1 and 3 mM.

The present invention also relates to a nucleotide sequence as defined above, characterized in that it comprises or is constituted by:

the nucleotide sequence SEQ ID NO: 3 or SEQ ID NO: 15 encoding SEQ ID NO: 4 or SEQ ID NO: 16 respectively, or any nucleotide sequence derived, by degeneration of the genetic code, from the sequence SEQ ID NO: 3 or SEQ ID NO: 15, and encoding a protein represented by SEQ ID NO: 4 or SEQ ID NO: 16 respectively, or any nucleotide sequence derived, in particular by substitution, suppression or addition of one or more nucleotides, from the sequence SEQ ID NO: 3 or SEQ ID NO: 15 encoding a protein derived from SEQ ID NO: 4 or SEQ ID NO: 16 respectively, or any nucleotide sequence homologous to SEQ ID NO: 3 or SEQ ID NO: 15, preferably having a homology of at least approximately 60%, with the sequence SEQ ID NO: 3 or SEQ ID NO: 15, or any fragment of the nucleotide sequence SEQ ID NO: 3 or SEQ ID NO: 15 or of the nucleotide sequences defined above, said fragment preferably being made up of at least approximately 180 nucleotides, and in particular of at least approximately 480 contiguous nucleotides in said sequence, or any nucleotide sequence complementary to the abovementioned sequences or fragments, or any nucleotide sequence capable of hybridizing under stringent conditions with the sequence complementary to one of the abovementioned sequences or fragments.

The present invention also relates to a nucleotide sequence as defined above, characterized in that it comprises or is constituted by:

the nucleotide sequence SEQ ID NO: 5 or SEQ ID NO: 17 encoding SEQ ID NO: 6 or SEQ ID NO: 18 respectively, or any nucleotide sequence derived, by degeneration of the genetic code, from the sequence SEQ ID NO: 5 or SEQ ID NO: 17, and encoding a protein represented by SEQ ID NO: 6 or SEQ ID NO: 18 respectively, or any nucleotide sequence derived, in particular by substitution, suppression or addition of one or more nucleotides, from the sequence SEQ ID NO: 5 or SEQ ID NO: 17 encoding a protein derived from SEQ ID NO: 6 or SEQ ID NO: 18 respectively, or any nucleotide sequence homologous to SEQ ID NO: 5 or SEQ ID NO: 17, preferably having a homology of at least approximately 60%, with the sequence SEQ ID NO:5 or SEQ ID NO: 17, or any fragment of the nucleotide sequence SEQ ID NO: 5 or SEQ ID NO: 17 or of the nucleotide sequences defined above, said fragment preferably being made up of at least approximately 180 nucleotides, and in particular of at least approximately 480 contiguous nucleotides in said sequence, or any nucleotide sequence complementary to the abovementioned sequences or fragments, or any nucleotide sequence capable of hybridizing under stringent conditions with the sequence complementary to one of the abovementioned sequences or fragments.

The present invention also relates to a nucleotide sequence as defined above, characterized in that it comprises or is constituted by:

the nucleotide sequence SEQ ID NO: 7 or SEQ ID NO: 19 encoding SEQ ID NO: 8 or SEQ ID NO: 20 respectively, or any nucleotide sequence derived, by degeneration of the genetic code, from the sequence SEQ ID NO: 7 or SEQ ID NO: 19, and encoding a protein represented by SEQ ID NO: 8 or SEQ ID NO: 20 respectively, or any nucleotide sequence derived, in particular by substitution, suppression or addition of one or more nucleotides, from the sequence SEQ ID NO: 7 or SEQ ID NO: 19 encoding a protein derived from SEQ ID NO: 8 or SEQ ID NO: 20 respectively, or any nucleotide sequence homologous to SEQ ID NO: 7 or SEQ ID NO: 19, preferably having a homology of at least approximately 60%, with the sequence SEQ ID NO: 7, or any fragment of the nucleotide sequence SEQ ID NO: 7 or SEQ ID NO: 19 or of the nucleotide sequences defined above, said fragment preferably being made up of at least approximately 180 nucleotides, and in particular of at least approximately 480 contiguous nucleotides in said sequence, or any nucleotide sequence complementary to the abovementioned sequences or fragments, or any nucleotide sequence capable of hybridizing under stringent conditions with the sequence complementary to one of the abovementioned sequences or fragments.

The present invention also relates to a nucleotide sequence as defined above, characterized in that it comprises or is constituted by:

the nucleotide sequence SEQ ID NO: 9 encoding SEQ ID NO: 10, or any nucleotide sequence derived, by degeneration of the genetic code, from the sequence SEQ ID NO: 9, and encoding a protein represented by SEQ ID NO: 10, or any nucleotide sequence derived, in particular by substitution, suppression or addition of one or more nucleotides, from the sequence SEQ ID NO: 9 encoding a protein derived from SEQ ID NO: 10, or any nucleotide sequence homologous to SEQ ID NO: 9, preferably having a homology of at least approximately 60%, with the sequence SEQ ID NO: 9, or any fragment of the nucleotide sequence SEQ ID NO: 9 or of the nucleotide sequences defined above, said fragment preferably being made up of at least approximately 180 nucleotides, and in particular of at least approximately 480 contiguous nucleotides in said sequence, or any nucleotide sequence complementary to the abovementioned sequences or fragments, or any nucleotide sequence capable of hybridizing under stringent conditions with the sequence complementary to one of the abovementioned sequences or fragments.

The present invention also relates to a nucleotide sequence as defined above, characterized in that it comprises or is constituted by:

the nucleotide sequence SEQ ID NO: 11 encoding SEQ ID NO: 12, or any nucleotide sequence derived, by degeneration of the genetic code, from the sequence SEQ ID NO: 11, and encoding a protein represented by SEQ ID NO: 12, or any nucleotide sequence derived, in particular by substitution, suppression or addition of one or more nucleotides, from the sequence SEQ ID NO: 11 encoding a protein derived from SEQ ID NO: 12, or any nucleotide sequence homologous to SEQ ID NO: 11, preferably having a homology of at least approximately 60%, with the sequence SEQ ID NO: 11, or any fragment of the nucleotide sequence SEQ ID NO: 11 or of the nucleotide sequences defined above, said fragment preferably being made up of at least approximately 180 nucleotides, and in particular of at least approximately 800 contiguous nucleotides in said sequence, or any nucleotide sequence complementary to the abovementioned sequences or fragments, or any nucleotide sequence capable of hybridizing under stringent conditions with the sequence complementary to one of the abovementioned sequences or fragments.

The present invention relates to a preparation method as defined above, for nucleotide sequences encoding the protein chains constituting the haemoglobin molecule of Annelida, in particular of *Arenicola marina*, said method being characterized in that it comprises the following stages:

a stage of bringing together the abovementioned haemoglobin molecule with at least one dissociating agent and a reducing agent, in particular a mixture made up of dithiothreitol (DTT) or tris(2-carboxyethyl)phosphine hydrochloride (TCEP) or beta-mercaptoethanol and a dissociation buffer, for a sufficient time to separate the protein chains from each other, allowing the dissociation, then the reduction of said haemoglobin molecule, in order to obtain the protein chains constituting said molecule, the isolation of the abovementioned protein chains, the microsequencing by mass spectrometry and Edman sequencing of each of the abovementioned isolated protein chains, in order to obtain a microsequence corresponding to each of the sequences made up of 5 to 20 amino acids, the determination of the degenerated primer pairs (sense and antisense) from the abovementioned microsequences, the preparation of the nucleotide sequences encoding the abovementioned protein chains, from the primers as obtained previously, by a polymerase chain amplification method (PCR), comprising the following stages:

the first stage of said method is a stage of denaturation of the cDNA encoding the protein chains constituting the haemoglobin molecule of *Arenicola marina*, of approximately 10 seconds to approximately 5 minutes at a temperature comprised between approximately 90° C. and approximately 110° C., the cycle, repeated approximately 30 to 40 times, comprises the following stages:

a stage of denaturation of the cDNA encoding the protein chains constituting the haemoglobin molecule of *Arenicola marina*, of approximately 10 seconds to approximately 5 minutes, at a temperature comprised between approximately 90° C. and approximately 110° C., a stage of hybridization of the primer pairs of the invention to the abovementioned strands of monocatenary cDNA in order to obtain hybridized primers, of approximately 20 seconds to approximately 2 minutes, at a temperature comprised between approximately 50° C. and approximately 56° C., a stage of elongation of the hybridized primers as obtained previously by a polymerase of approximately 20 seconds to approximately 1 minute and 30 seconds, at a temperature comprised between approximately 70° C. and approximately 75° C., and the last stage of the method is a stage of elongation of the hybridized primers as obtained previously by a polymerase of approximately 5 minutes to approximately 15 minutes at a temperature comprised between approximately 70° C. and approximately 75° C.

EXPERIMENTAL PART

Figure 1:
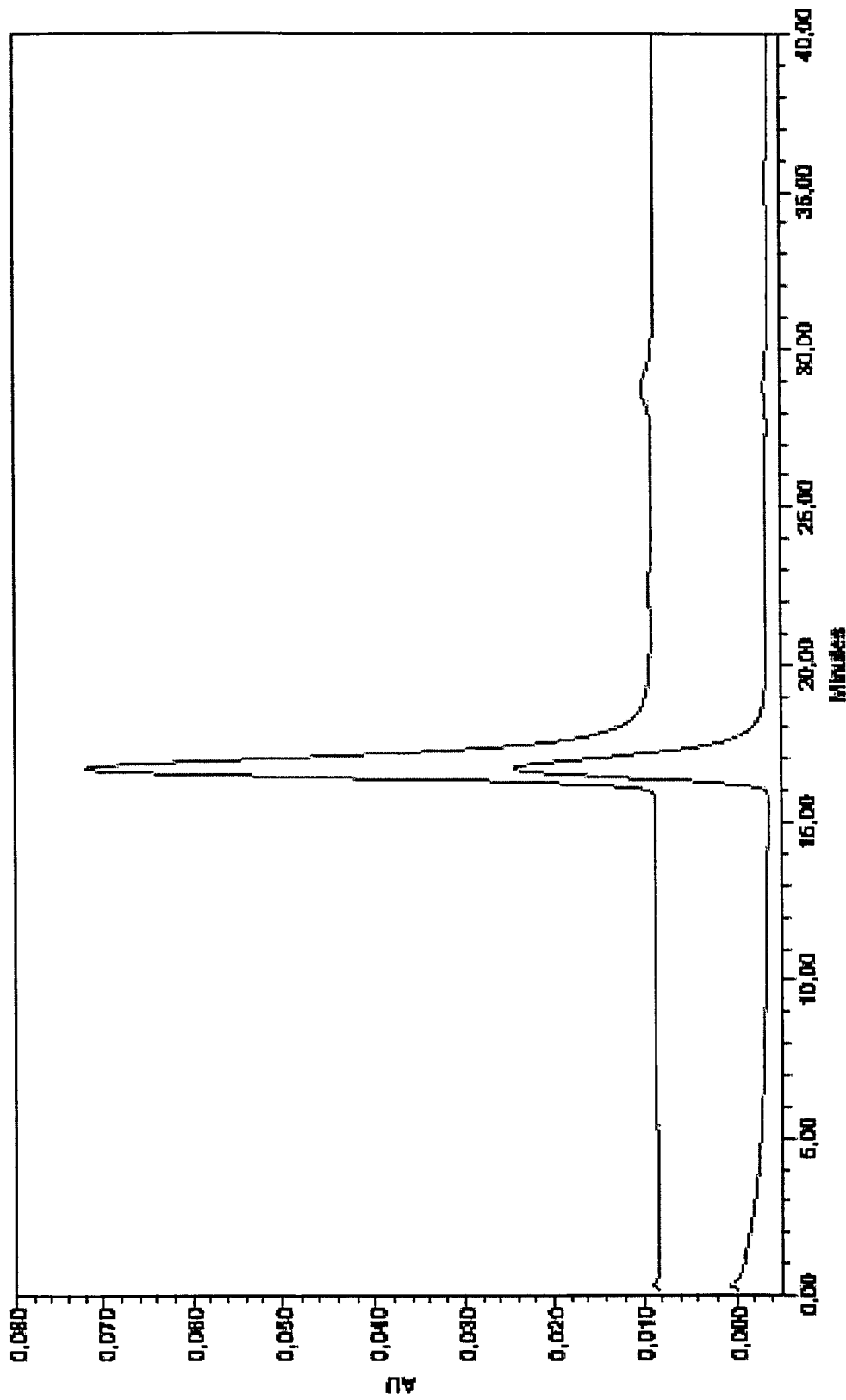
FIG. 1 represents a chromatogram of the haemoglobin of *Arenicola marina* on a Superose 12-C column. The upper curve corresponds to an absorbance of 414 nm and the lower curve to an absorbance of 280 nm. (The collector is programmed to collect between 16 and 18 minutes).

An objective of the present invention is the use of the extracellular haemoglobin of the marine polychaete *Arenicola marina* (HbAm) as a blood substitute in vertebrates. However, even if this worm represents a significant biomass, synthesis by genetic engineering has proved to be an indispensable and necessary route. It is therefore of prime importance to obtain the primary sequences of the protein chains constituting HbAm in order to develop an artificial, functional and stable haemoglobin from the self-assembly properties of this molecule. The dissociation protocols of each sub-unit and reduction to polypeptide chains, as well as the purification, isolation, microsequencing and sequencing techniques of these chains are discussed in detail hereafter.

Extraction and Purification of the Haemoglobin

1) Species Studied: *Arenicola marina*; Annelida of the Intertidal Ecosystem

The Annelida Polychaete *Arenicola marina* is a sedentary species widespread throughout all the coasts of the North Atlantic, Black Sea and Adriatic situated above the fortieth parallel. In the Roscoff region, the *Arenicola*, commonly known in French as the "ver du pêcheur" forms dense populations. The sediment inhabited by these populations has an irregular surface of alternating bumps and hollows formed respectively by mounds of coprogenous particles and conical depressions. The *Arenicola* lives in galleries made in the sand. The structure of the gallery is presented in the shape of a U, with an open branch on the outside, the other being closed. The *Arenicola* is accommodated in the horizontal part, its cephalic end oriented towards the blind part. It ingests the sand, extracts the assimilable organic matter and then defecates through its caudal end, thus forming of the mounds of wormcasts of sand. Inside the mediolittoral stage, the distribution and density of the populations are essentially controlled by the granulometry, the concentration of organic matter and the salinity.

The *Arenicola*, living above all in the tidal zones, has to undergo variations in oxygen pressure. Its gallery makes it possible for it to be in permanent contact with seawater (rich in oxygen) at low tide.

2) Methods of Study 2.1. Sampling of the Biological Material

The animals are collected at low tide, in the Baie de Penpoull, near Roscoff (France) and kept in seawater overnight in order to empty their digestive tube. The blood samples are taken from the dorsal vessel using a syringe. The samples are collected on ice and filtered through glass wool. After low-temperature centrifugation (15,000 g for 15 min at 4° C.) in order to avoid the dissociation of the molecules and eliminate the tissue debris, the supernatants are concentrated by means of an Amicon cell (Millipore) and a "cut-off" membrane of 500 kDa (only masses greater than 500 kDa are retained).

2.2. Purification of the Haemoglobins

Once the blood is concentrated, a low-pressure filtration (FPLC) by exclusion (separation as a function of the size of the molecule: the more significant the size of the molecule the more rapidly it is eluted) is carried out on a column (100×3 cm) of Sephacryl S-400 gel (Amersham)(separation range comprised between $20 \times 10^3$ and $8000 \times 10^3$), in a cold room (4° C.). Each purification is carried out on 5 mL of sample, eluted with the *Arenicola marina* salinated buffer (10 mM Hepes; 4 mM KCl; 145 mM NaCl; 0.2 mM $MgCl_2$ adjusted to pH 7.0 with 2N soda). The flow rate used for this first purification is 40 r.p.m. and only the first, reddest, fraction (containing heme) is recovered. This fraction is then concentrated using a Centricon-10 kDa tube retaining the molecules with a weight greater than or equal to 10,000 Da.

A second purification is then carried out by low-pressure filtration (HPLC System, Waters) of 200 µL aliquots on a 1×30 cm Superose 12-C column (Pharmacia, separation range comprised between $5 \times 10^3$ and $3 \times 10^5$ Da) at ambient temperature. The flow rate used is 0.5 ml/min. The samples are kept at 4° C. and collected in ice. The absorbance of the eluate is monitored at two wavelengths: 280 nm (absorbance peak characteristic of proteins) and 414 nm (absorbance peak characteristic of heme). The fractions containing heme are isolated using a collector (programmed on a time window corresponding to the retention time of the haemoglobin) (FIG. 1). The samples are concentrated, assayed, then stored at −40° C. before use.

2.3. Assay of the Haemoglobins

Drabkin's reagent (Sigma), used for the assay, makes it possible to determine the quantity of heme in the solution. The haemoglobin reacts with Drabkin's reagent which contains potassium ferricyanide, potassium cyanide and sodium bicarbonate. The haemoglobin is converted to methaemoglobin by the action of the ferricyanide. The methaemoglobins then react with the cyanide in order to form cyanmethaemoglobin. The absorbance of this derivative at 540 nm is proportional to the quantity of heme in the solution. The extracellular haemoglobin of *Arenicola marina* (HBL) contains on average 1 mol of heme per 23,000 g of protein, which makes it possible by a simple calculation, to obtain the HBL concentration of each sample.

3) Results

Figure 2:
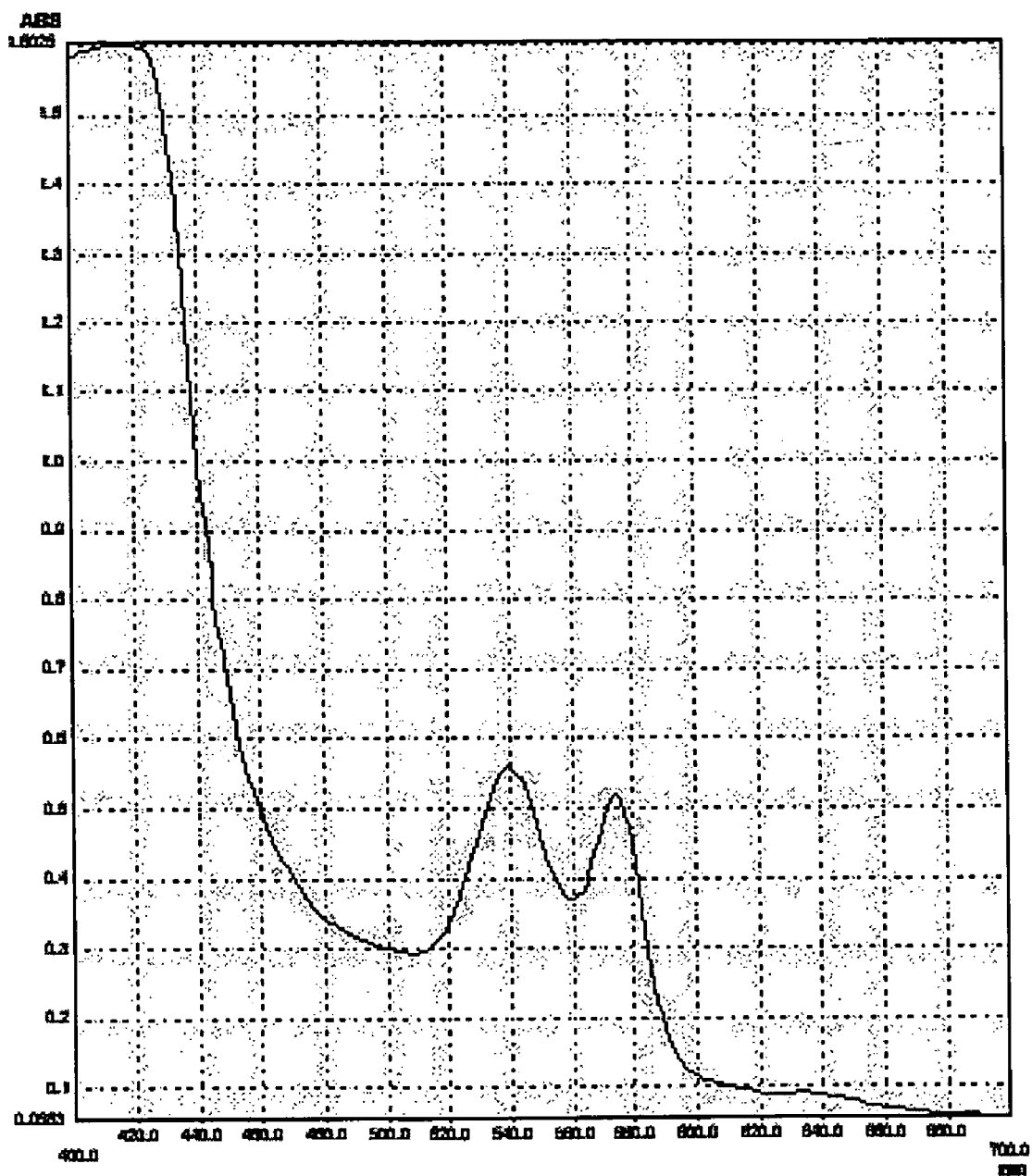
FIG. 2 represents the UV spectrum of the functional haemoglobin of *Arenicola marina* (in its oxyhaemoglobin form).

Thus, several milligrams of extracellular haemoglobin of *Arenicola marina* were purified. Each batch (1 mL aliquots) is analyzed by FPLC on a Superose 12-C column (Pharmacia) in order to ensure the purity of the sample (a single peak). Similarly a UV spectrum over a range of 400 nm to 700 nm is produced in order to verify the functionality of the haemoglobins of each batch (FIG. 2). Three absorption maxima are observed at 414, 541 and 577 nm. By comparison, it should be recalled that the methaemoglobin exhibits two maxima at 500 and 635 nm.

Finally, these batches are used by Biotrial S.A. (Rennes, France) for preclinical tests carried out on mice and rats in order to test the possible pathological and immunogenic reactions.

Dissociation of the Extracellular Haemoelobin of *Arenicola marina* in These Different Basic Sub-Units (Trimers, Linker Dimers and Monomers)

The dissociation of the extracellular haemoglobin of *Arenicola marina* (HbAm) must be total and retain the functional sub-units. The different sub-units are then isolated and analyzed by the liquid chromatography technique (exclusion and ion exchange), developed for this purpose.

1) Dissociation of the HBL 1.1. Dissociation Protocol

The preliminary studies of dissociation were developed from the publications of the prior art (Vinogradov et al., 1979; Sharma et al., 1996; Mainwaring et al., 1986; Polidori et al., 1984; Kapp et al., 1984; Chiancone et al., 1972; Vinogradov et al., 1991; Krebs et al., 1996), i.e. in the presence of a single dissociating reagent: urea, heteropolytungstate ions, guanidinium salts, SDS or hydroxide ions. The agents used act differently on the molecule:

the hydroxide ions (OH$^-$), the SDS, the guanidinium salts and the heteropolytungstate ions destabilize the salt bridges the urea destabilizes the hydrophobic interactions The aim is to obtain the four basic sub-units as rapidly and effectively as possible, hence the idea of combining the different dissociating agents and in particular the alkaline pH and urea. After different tests, it emerges that a rapid and effective dissociation is obtained with 3M urea diluted in the dissociation buffer (0.1 M of Trisma base and 1 mM of EDTA) adjusted to pH 10 with 2N soda. The HbAm is adjusted to a concentration of approximately 4 mg/mL (stock solution). All the analyses are carried out at +4° C. and the samples are kept in the dark throughout the study. (Trisma=tris[hydroxymethyl]aminomethane)

1.2. Exclusion Chromatography Analyses

The analysis conditions are shown in detail in Table 1 below.

| | |
|---|---|
| System HPLC | HPLC Waters 626 LC System |
| Column | Superose 12-C (Pharmacia) |
| | (separation range comprised between |
| | $5 \times 10^3$ and $3 \times 10^5$ Da) |
| Flow rate | 0.5 mL/min |

-continued

| | |
|---|---|
| Eluent | buffer pH 7.0 |
| | (buffered for example with |
| | concentrated hydrochloric acid) |
| | and filtered through a 0.22 μm (or 0.45 μm) filter |
| Temperature of the injecter | +4° C. |

| | Sample | |
|---|---|---|
| | Analytic monitoring | Separation and collection |
| Volume injected | 20 μL | 200 μL |
| Preparation of the samples | Stock solution diluted to 1 mg/mL in the dissociation buffer at pH 10 and filtered through 0.45 μm | Stock solution filtered through a 0.45 μm filter |

1.3. Ion-Exchange Analyses

The isoelectric point (pHi) of HBL being 4.69 (Vinogradov, 1985), ion-exchange analysis is carried out on a CIM DEAE disk anionic column (Interchim). In fact, HBL is negatively charged for a pH greater than the pHi and is therefore fixed on a positively charged resin (DEAE resin). The elution is carried out by means of the ionic force with a non-linear NaCl gradient of 0 to 1 M (1 M NaCl solution diluted in the dissociation buffer at pH 7.0 and filtered through 0.45 μm). The dissociation buffer at pH 7 is used as elution buffer. The flow rate is 4 mL/min.

1.4. Reversed-Phase Chromatography Analyses

Reversed-phase chromatography is carried out on a Waters 300 $C_{18}$ 5 μm (4.6×250 mm) Symmetry column. In the presence of acetonitrile and TFA (trifluoroacetic acid), HbAm is dissociated into its basic sub-units (Trimer, Monomer and Linker) and the heme is dissociated from the globins. Thus, without previous treatment, HbAm is dissociated at the column head. The method developed is described in the table below.

| | |
|---|---|
| flow rate | 1 mL/min |
| Eluent A | H$_2$O MilliQ + 0.1% v/v HFBA |
| Eluent B | ACN + 0.1% v/v HFBA |

| | Gradient | |
|---|---|---|
| Time in min | % A | % B |
| 0 | 58 | 42 |
| 40 | 50 | 50 |
| 41 | 48 | 52 |
| 90 | 47 | 53 |
| 95 | 5 | 95 |
| 110 | 5 | 95 |

2) Results 2.1. Exclusion Chromatography

Figures 3, 4:
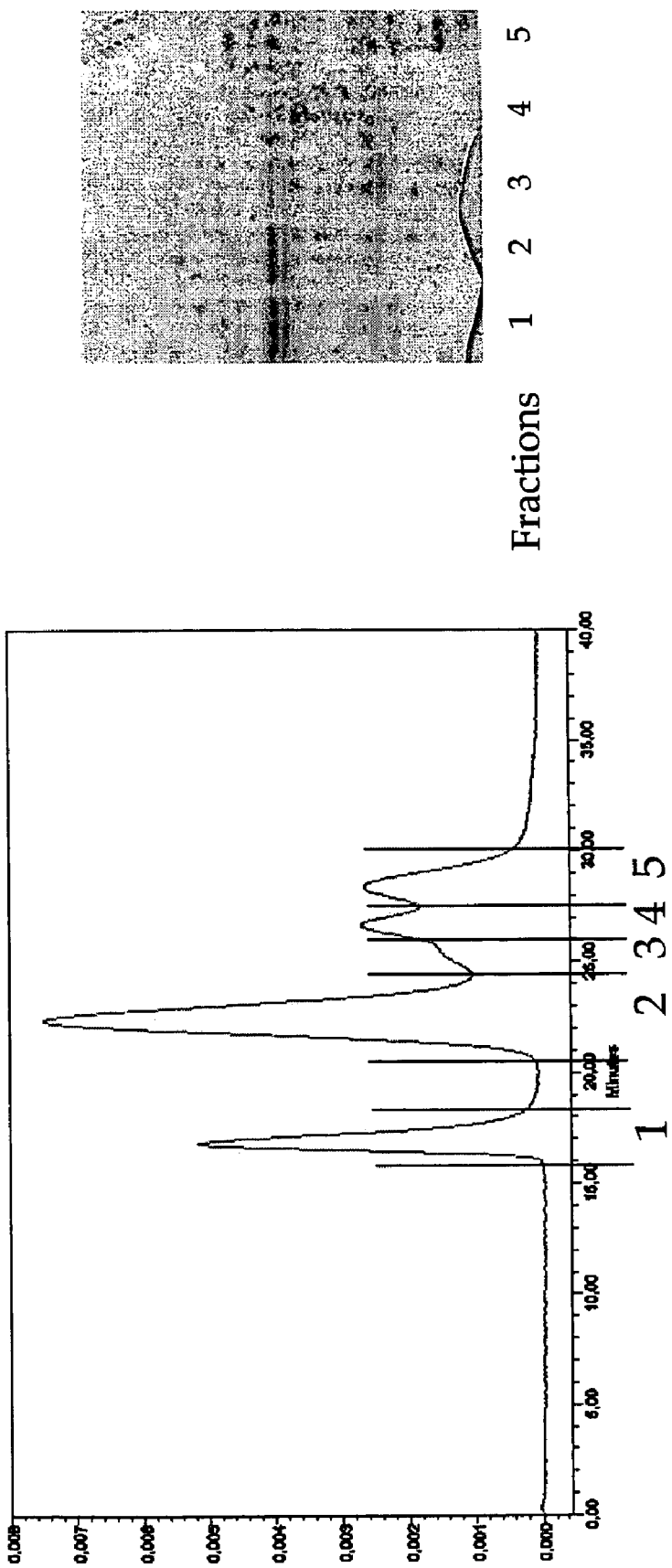
FIG. 3 represents the chromatogram (at 414 nm) of the (partially) dissociated HbAm obtained on Superose 12-C and the vertical lines on the chromatogram correspond to the collecting windows (corresponding to the recovery of the sub-units).
FIG. 4 represents an SDS-PAGE gel obtained for the different fractions collected.

The chromatogram of the partly dissociated HbAm is represented in FIG. 3. Five peaks are observed and have to be identified. The molecules are eluted according to their decreasing mass and the eluted native HbAm in the hold-up volume (16 min). The fractions corresponding to each peak are analyzed by SDS-PAGE (FIG. 4). The results are presented in Table 2 below.

| Fractions | Retention time | Sub-units |
|---|---|---|
| 1 | 16 min 40 | Native HbAm |
| 2 | 22 min 20 | Dodecamer |
| 3 | 25 min 30 | Linker dimer |
| 4 | 26 min 40 | Trimer |
| 5 | 28 min 30 | Monomers |

2.2 Ion Chromatography

Figures 5, 6:
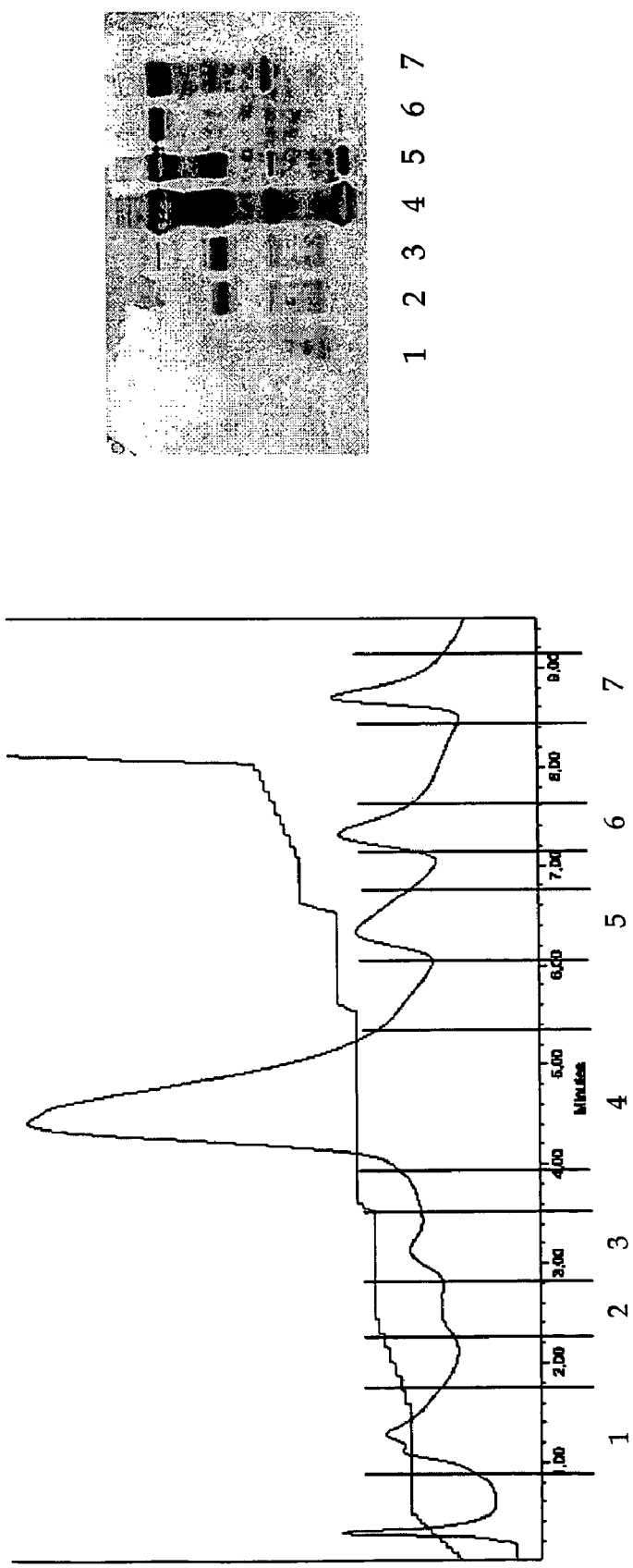
FIG. 5 represents the chromatogram (at 414 nm) of the (partially) dissociated HbAm obtained on CIM DISK DEAE (anionic exchange system) and the vertical lines on the chromatogram correspond to the collecting windows. The dotted curve indicates the gradient.
FIG. 6 represents an SDS-PAGE gel obtained for the different fractions collected.

Once the method has been developed (Table 3), the fractions are collected, concentrated and analyzed by SDS gel in order to identify each peak (FIG. 6 and Table 4).

A method is then developed for repurifying each sub-unit.

TABLE 3

Method developed for the analysis of the dissociated HBL on CIM-DEAE

| Time in min | A: 1M NaCl in B | B: Dissociation buffer pH 7.0 |
|---|---|---|
| 0 | 5% | 95% |
| 0.5 | 15% | 85% |
| 1.5 | 15% | 85% |
| 2.5 | 22% | 78% |
| 3.5 | 22% | 78% |
| 3.6 | 25% | 75% |
| 5.5 | 25% | 75% |
| 5.6 | 29% | 71% |
| 6.5 | 29% | 71% |
| 6.6 | 36% | 64% |
| 7.0 | 36% | 64% |
| 8.0 | 45% | 55% |
| 8.1 | 100% | 0% |
| 9.5 | 100% | 0% |

TABLE 4

Association carried out after analysis of the gel (FIG. 6) between the retention time and the sub-units.

| fractions | Retention time | Sub-units |
|---|---|---|
| 1 | 1 min 15 | Monomers |
| 2 | 2 min 40 | Linker dimer |
| 3 | 3 min 10 | Linker dimer |
| 4 | 4 min 40 | Dodecamer |
| 5 | 6 min 30 | ? |
| 6 | 7 min 30 | Trimer |
| 7 | 8 min 50 | HbAm |

2.3. Reversed-Phase Chromatography

Once the method has been developed, the fractions are collected, lyophilized and analyzed by mass spectrometry in order to identify each peak.

| fractions | Retention time | Sub-units |
|---|---|---|
| 1 | 12 min | Linker |
| 2 | 22 min | Linker |
| 3 | 34 min | Monomer a1 |
| 4 | 38 min | Monomer a2 |
| 5 | 50-70 min | Trimers |

The chemical properties of the trimers must be too close for it to be possible to separate them by reversed-phase. Thus, it has been possible to isolate only the two linkers and the monomers a1 and a2.

2.4. Dissociation of the HbAm

The dissociation kinetics are monitored by exclusion chromatography. The integration of the chromatograms by Millenium software (Waters) makes it possible to calculate the percentage of the different compounds from the area under the curve. The evolution of the dissociation kinetics is represented in FIGS. 7, 8 and 9.

Figure 7:
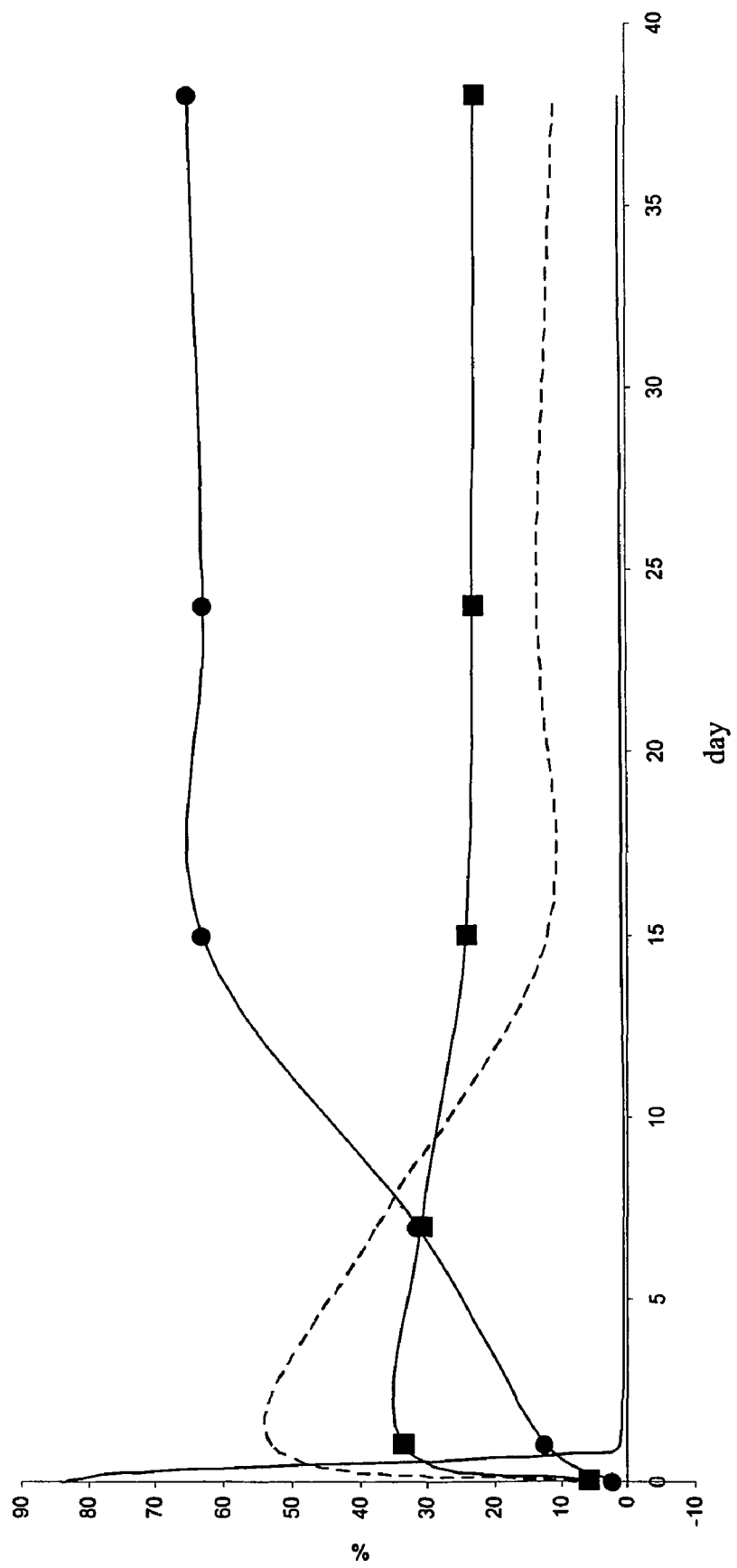
FIG. 7 represents the dissociation kinetics of the HbAm in the presence of 3M urea. The x-axis corresponds to the number of days and the y-axis corresponds to the percentage of dissociation of the native molecule; the dotted curve corresponds to the dodecamer; the curve with the black squares to the trimer and the "linker" (structural chain); the curve with the black circles to the monomers.
Figure 8:
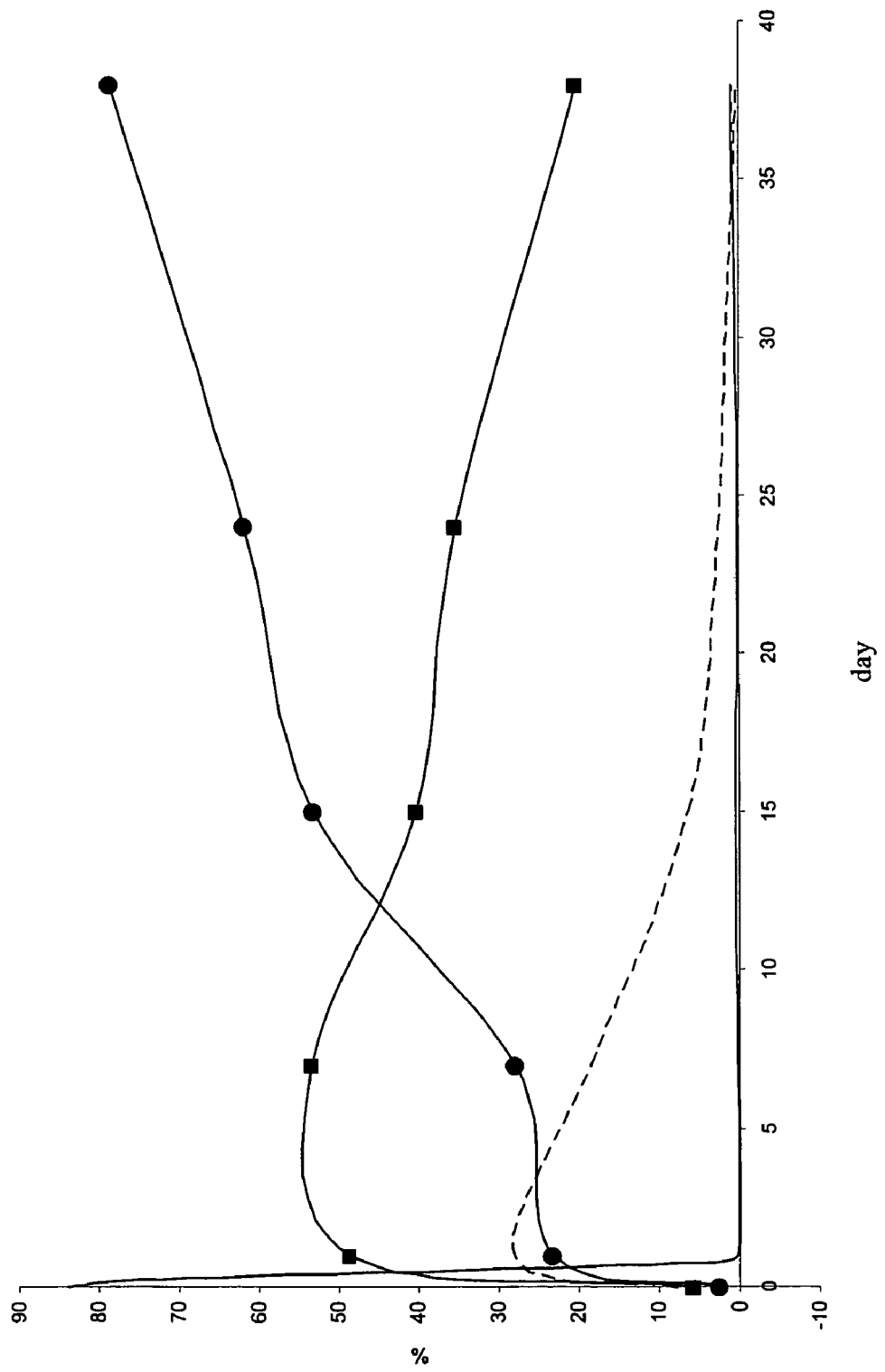
FIG. 8 represents the dissociation kinetics of the HbAm at pH 10. The x-axis corresponds to the number of days and the y-axis corresponds to the percentage of dissociation of the native molecule; the dotted curve corresponds to the dodecamer; the curve with the black squares to the trimer and the "linker"; the curve with the black circles to the monomers.
Figure 9:
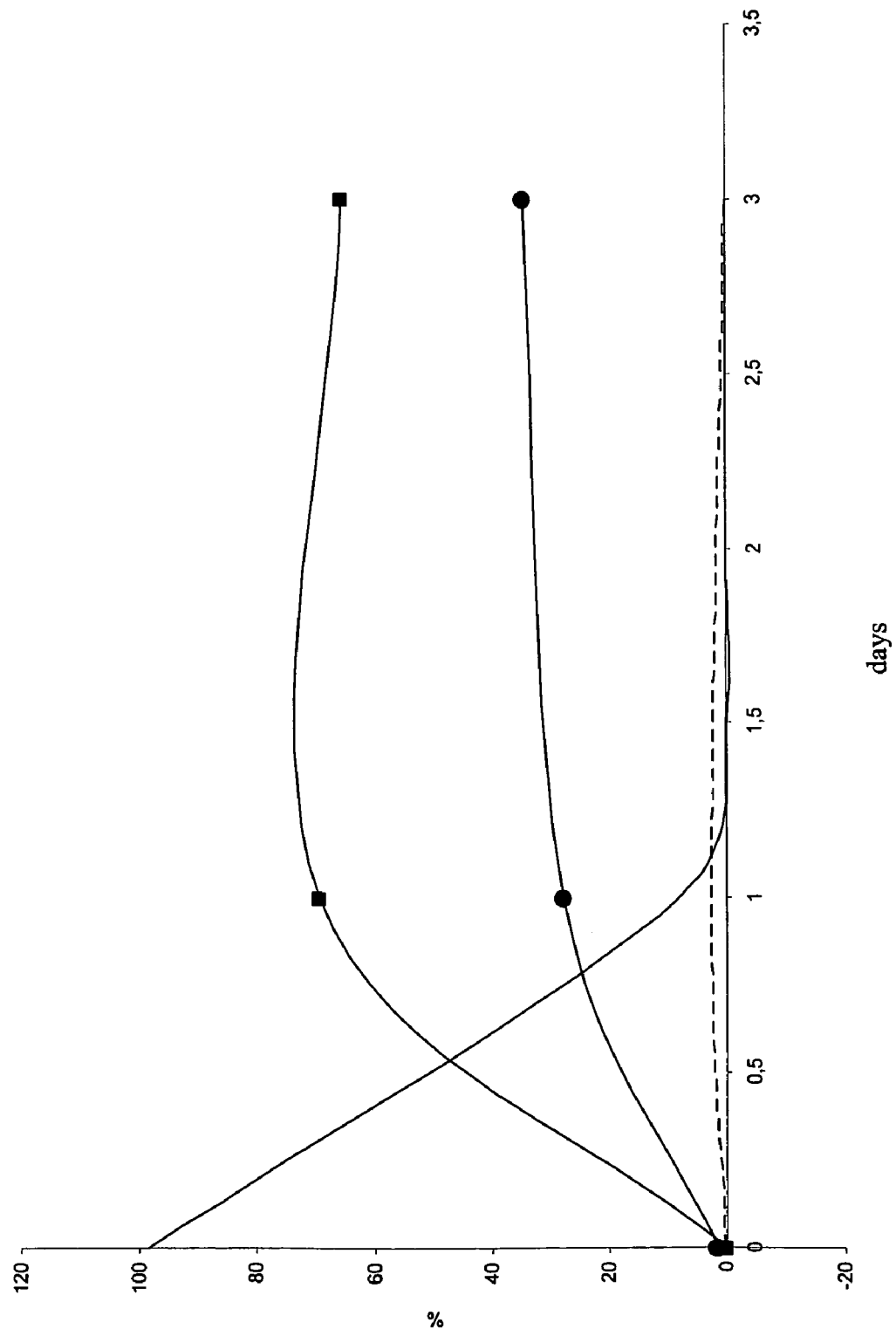
FIG. 9 represents the dissociation kinetics of the HbAm in the presence of 3M urea at pH 10. The x-axis corresponds to the number of days and the y-axis corresponds to the percentage of dissociation of the native molecule; the dotted curve corresponds to the dodecamer; the curve with the black squares to the trimer and the "linker"; the curve with the black circles to the monomers.

The three graphs in FIGS. 7, 8 and 9 show the benefit of combining the two dissociating agents (3 M urea and OH⁻) in order to effectively obtain the three basic sub-units in 24 hours.

Reassociation of the Haemoglobin

1) Materials and Methods

The reassociation experiments are carried out on dissociated HbAm according to the protocols mentioned above (pH9, pH10, 3M Urea, 4M Urea, 3M Urea at pH 10). Different reassociation buffers are tested in order to obtain an optimum reassociation. The change of buffer (dissociation buffer→reassociation buffer) is carried out in two different ways:

The dissociated HbAm is washed 4 times against 4 mL of reassociation buffer on Centricon-10 (Millipore) at +4° C.;

The dissociated HbAm is dialyzed for 24 hours against MilliQ water (Millipore) (2×2 L) then for 48 hours against the reassociation buffer (3×2 L) at +4° C.

2) Results

Figure 10:
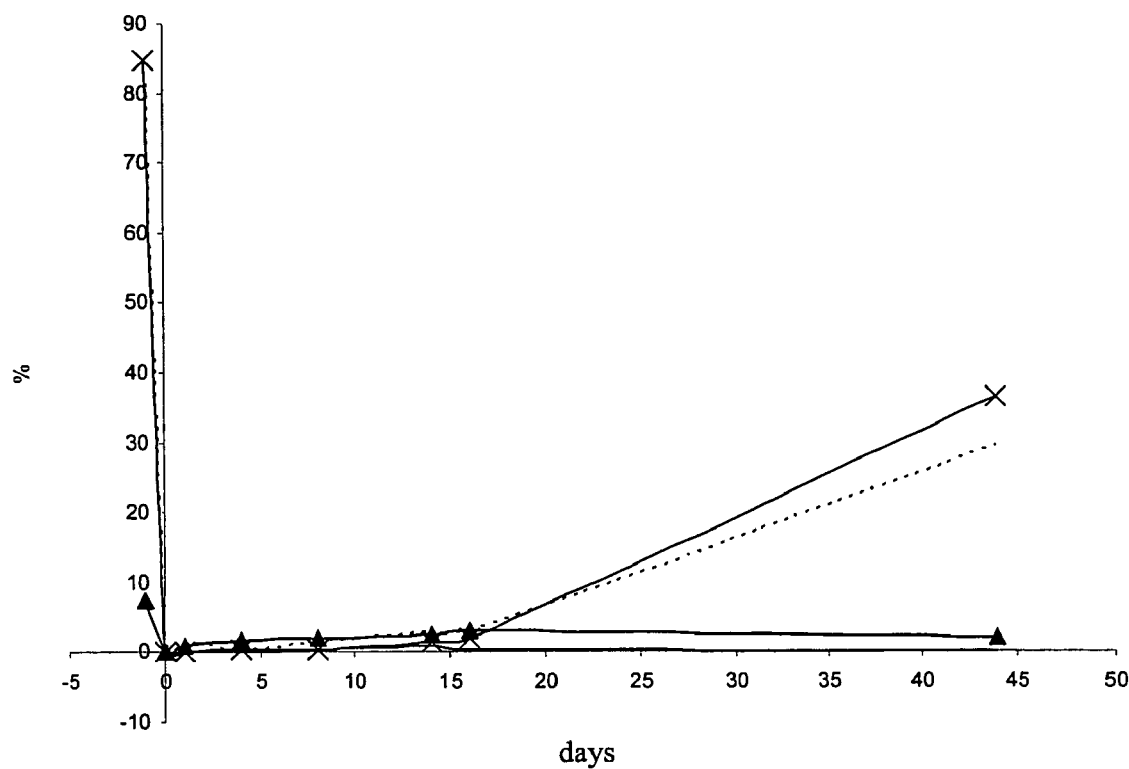
FIG. 10 represents the monitoring of the reassociation kinetics from the percentage of HbAm (HBL) and Dodecamer (D) and according to the buffer changing technique (Centricon or Dialysis). The x-axis corresponds to the number of days and the y-axis corresponds to the percentage of dissociation of the native molecule with the Centricon technique; the dotted curve corresponds to HBL with the dialysis technique; the curve with the black triangles corresponds to the dodecamer with the Centricon technique; the full line curve corresponds to the dodecamer with the dialysis technique.
Figure 11:
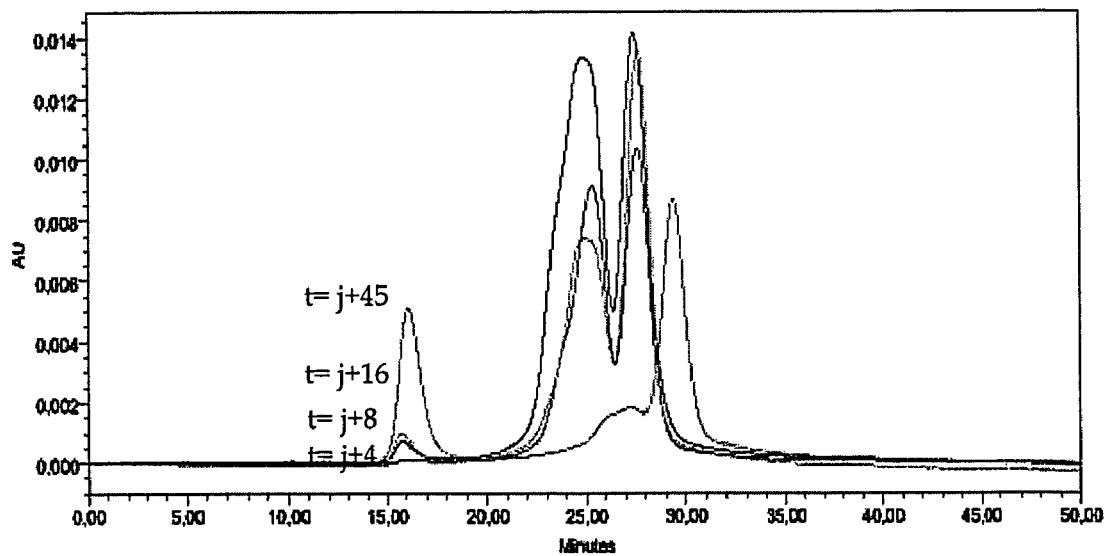
FIG. 11 represents the superposition of the exclusion chromatography chromatograms during the reassociation corresponding to different reassociation times.

According to subsequent results relating to the extracellular haemoglobins of Annelida (Mainwaring et al., 1986; Polidori et al., 1984), the presence of divalent ions such as $Ca^{2+}$ and $Mg^{2+}$ is necessary for maintenance of the quaternary structure of haemoglobin. In fact, they stabilize and slow down the dissociation phenomenon (Sharma et al., 1996). These ions form a complex with the carboxylate groups of the side chains and carbonyls of the main chains. The presence of divalent ions can have an effect on the reassociation when the carboxylic groups are ionized, therefore inter alia when the dissociation has taken place at an alkaline pH. It is therefore significant that the reassociation buffer contains calcium and/or magnesium. This also explains the presence of EDTA in the dissociation buffer; EDTA which chelates these divalent ions. The buffer now developed is made up of 0.1 M of Trisma base, 400 mM of NaCl, 2.95 mM KCl, 32 mM $MgSO_4$, 11 mM $CaCl_2$ adjusted to pH 7 with concentrated HCl. The reassociation is monitored according to the same principle as the dissociation (FIGS. 10 and 11).

A reassociation is observed if the dissociation is of short duration of the order of one minute. This reassociation corresponds to a rearrangement of dissociation intermediates which are truncated haemoglobins (HBL dissociated from 1 or more twelfths).

Reduction of HbAm for the Study of the Different Polypeptide Chains

1) Reduction of Haemoglobin Prior to Separation by Reversed-Phase Liquid Chromatography The HbAm (4 mg/mL) is reduced in 10% DTT (dithiothreitol) dissolved in a dissociation buffer at pH 8-9 (0.1 M trisma or 10 mM ammonium bicarbonate) for 30 minutes at ambient temperature. Once reduced, the protein chains obtained are alkylated in the presence of 100 mM iodoacetamide dissolved in a dissociation buffer at pH 8-9 for 30 minutes at ambient temperature.

The following protocol can also optionally be envisaged: The HbAm (4 mg/mL) is reduced in 100 mM of DTT (dithiothreitol) dissolved in the dissociation buffer at pH 8-9 for 1 hour at 40° C. Under these drastic conditions, only the globins can be analyzed. In fact, the linkers (non-globin proteins) are rich in cysteines and are therefore damaged. Once reduced, the HbAm is washed 4 times on Amicon 30,000 Da (Millipore) only the filtrate of which is recovered (all which has a weight of less than 30,000 Da). The filtrate is then washed on Amicon 10,000 Da in order to eliminate all which is less than 10,000 Da. Thus, only the monomers comprised between 30,000 Da and 10,000 Da are contained in the sample (weight range of the globin chains which constitute HbAm).

Figure 12:
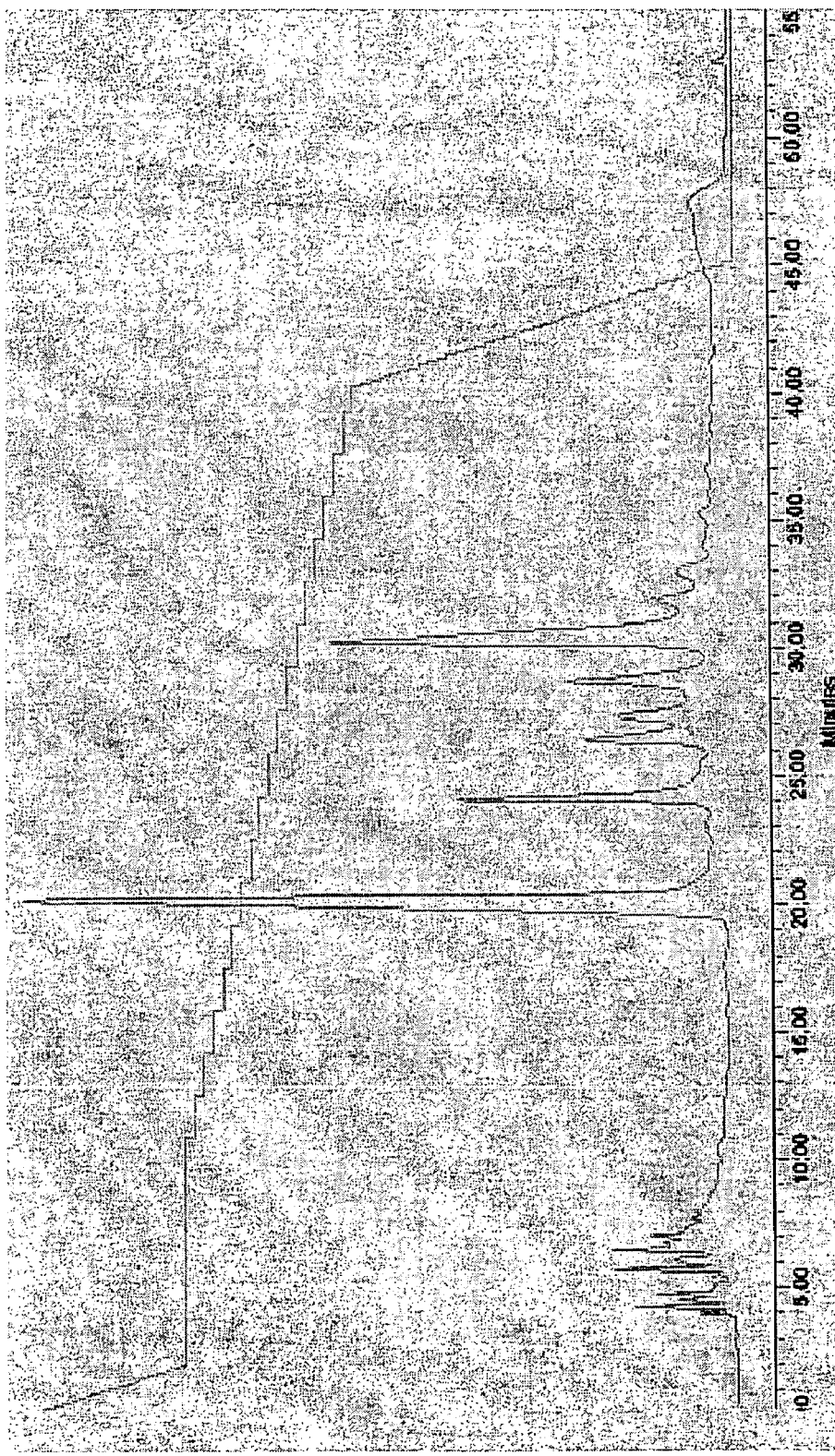
FIG. 12 represents the HPLC chromatogram obtained after separation of the polypeptide chains by Reversed-phase on a Symmetry C18 column (Waters). The codes (d2, a1, a2, b2, c) correspond to the names of the globins as mentioned in the article by Zal et al. (1997).

2) Separation of the Protein Chains by Reversed-Phase Chromatography 2.1 Materials and Methods Reversed-phase chromatography is carried out on a Waters Symmetry 300 $C_{18}$ 5 μm (4.6×250 mm) column. The method developed is described in the table below and the chromatogram obtained is represented in FIG. 12.

| flow rate | 1 mL/min |
| --- | --- |
| Eluent A | $H_2O$ MilliQ + 0.1% v/v HFBA |
| Eluent B | ACN + 0.1% v/v HFBA |

| Gradient | | |
| --- | --- | --- |
| Time in min | % A | % B |
| 0 | 75 | 25 |
| 2 | 58 | 42 |
| 10 | 58 | 42 |
| 40 | 40 | 60 |
| 45 | 0 | 100 |
| 55 | 0 | 100 |

The following protocol can also be optionally envisaged.

| flow rate | 1 mL/min |
| --- | --- |
| Eluent A | $H_2O$ MilliQ + 0.1% v/v TFA |
| Eluent B | ACN + 0.1% v/v TFA |

| Gradient | | |
| --- | --- | --- |
| Time in min | % A | % B |
| 0 | 80 | 20 |
| 0.25 | 60 | 40 |
| 4.0 | 55 | 45 |
| 10.0 | 55 | 45 |
| 10.05 | 0 | 100 |
| 16.0 | 0 | 100 |

Each protein chain (revealed by a single peak at 280 nm) is collected then lyophilized and stored at −40° C. until the next analyses. Thus, it has been possible to separate the following 5 monomers: $a_1$ (~15952 kDa), $a_2$ (~15975 kDa), $d_2$ (~17033 kDa), $b_2$ (~16020 kDa) and c (~16664 kDa).

3) Separation of the Protein Chains by Two-Dimensional Gel

Two-dimensional gel which is a combination of the isoelectric focusing technique in the first dimension and SDS-PAGE technique in the second dimension makes it possible to separate a complex protein mixture.

Isoelectric Focusing

After purification by FPLC, the haemoglobin of *Arenicola* is dialyzed and lyophilized. 500 μg are taken up in a rehydration buffer. This buffer contains 4% Chaps (3-[(3-cholamidopropyl)dimethylammonio]-1-propane-sulphonate; Sigma), 1% freshly prepared DTT, a cocktail of protease inhibitors (Bohringher), 50 μg/ml of TLCK (trypsin inhibitor) and 1 μl of 1% Bromophenol Blue.

The mixture is sonicated and centrifuged in order to eliminate the non-dissolved material. Stone oil is then applied to the two ends of the support of the isoelectric focusing band, and the sample is then applied to the medium. The 17 cm band is then applied to the sample, eliminating any air bubbles. The band is then covered with stone oil in order to avoid evaporation of the sample.

An active rehydration is then carried out at 50V (20° C. over 12 hours). The focalization is then carried out over two days.

The band is then recovered and placed on a 6-18% acrylamide gel, in particular 10%, 18 cm wide, 20 cm long and 1 mm thick. The migration is carried out in a refrigerated enclosure at 10° C., over 14 hours at 400 V, 25 mA and 100 W.

The separation of the protein chains is then carried out as a function of their size after sealing the band on top of the gel using a 1% agarose solution. Once separated, the protein bands are revealed on gel by staining with Coomassie blue (Coomassie® G250).

Construction of the Gradient Gel

Twenty-five ml of 18% polyacrylamide dense solution (2.5 M acrylamide; 0.4 M Tris; 30% Glycerol (v/v); 3.5 mM sodium dodecyl sulphate (SDS); 0.05% TEMED (N,N,N',N'-tetramethylethylenediamine; Sigma) (v/v); 1.6 mM sodium persulphate) are placed in a mixing chamber under constant stirring whilst the same volume of 6% polyacrylamide light solution (acrylamide 0.8 M; Tris 0.4 M; SDS 3.5 mM; TEMED 0.06% (v/v); sodium persulphate 2.4 mM) is placed in the other chamber. The top of the gel is covered with a saturated isobutanol solution in bidistilled water. The gel is then left for 1 hour to polymerize at ambient temperature, then the top of the gel is rinsed several times with bidistilled water and the whole is placed overnight at 10° C. After removal of the residual water using an absorbent paper, the concentration gel solution (0.56 M acrylamide; 6.9 mM methylene bis-acrylamide; 124 mM Tris; 3.5 mM SDS; 0.05% TEMED (v/v); 2.2 mM sodium persulphate) is poured onto the separation gel and a shim making it possible to form the blot of the band is introduced into the concentration gel solution. The polymerization is complete after 1 hour at ambient temperature.

4) Analysis by Micro Sequencing of the Isolated Protein Chains by Reversed-Phase and Two-Dimensional Gel The protein chains isolated by reversed-phase chromatography and by two-dimensional gel are then digested and analyzed by LC-MS/MS mass spectrometry on an ESI-Q-TOF type device.

Digestion of the Separated Proteins by Reversed-Phase Chromatography.

Each isolated protein chain is subjected to enzymatic digestion, an essential stage before their analysis by microsequencing. The lyophilized protein chains are dissolved in a milliQ water solution, acetonitrile containing endoprotease; trypsin which hydrolyzes at the C-terminal level of lysine and arginine, generally producing peptides with masses comprised between 500 and 2500 Da, over a minimum of 3 hours at ambient temperature.

Digestion of the Separated Proteins on Two-Dimensional Gel

Each spot of the gel is cut out in order to be subjected to enzymatic digestion. This enzymatic digestion stage is essential. It consists of hydrolyzing the proteins in a specific manner, using an enzyme, into several peptides.

Before beginning digestion, discoloration, reduction and alkylation stages are indispensable:

successive washings with ammonium hydrogen carbonate ($NH_4HCO_3$) and acetonitrile (ACN) make it possible to eliminate the staining agent present in the piece of gel, the reduction reactions with dithiothreitol (DTT) and alkylation reactions with iodoacetamide allow the opening then the blocking of the disulphide bridges formed between two cysteines present in the protein sequence and cysteine-acrylamide bonds.

The last stage of the method consists of extracting the trypsic peptides from the gel using an extraction solution, composed of acetonitrile and water, with a little acid added.

Analysis by NanoLC-MS-MS

The extracted peptides are then transferred to the PCR plate. This transfer is carried out with twice 15 μL, in order to recover all of the volume. In order to eliminate the acetonitrile, which could impede the retention of the peptides on the pre-column, a time of evaporation (pause) of 2 hours is applied before analysis by nanoLC-MS-MS.

Results

This made it possible to obtain a few hundred micosequences corresponding to each separate chain protein by 2D gel.

5) Analysis by Edman Sequencing of the Isolated Protein Chains by Reversed-Phase Chromatography Principle In the presence of N-methyl piperidine buffer, Phenyl-Iso-Thio-Cyanate (PITC) is coupled to the primary and secondary amine functions of the proteins (PTC-Protein). The reaction time at 45° C. is 18 minutes. The following peptide bond is weakened, which allows it to be cut in 3 minutes by pure trifluoroacetic acid (TFA) thus generating the anilino-thiazolinone (ATZ) of the first amino acid (AA) and the protein having lost the 1st AA.

The ATZ-AA is extracted from the reaction medium and converted in acid medium (25% TFA in water) to the more stable phenyl thio-hydantoin (PTH-AA). The PTH-AA can therefore be analyzed by HPLC and its nature determined by means of a PTH-AA standard. The reaction cycle can be repeated and thus leads to the protein sequence. Edman automated the reaction which bears his name by creating the first protein sequencer in 1967. The device is coupled to an HPLC into which it injects PTH-AA. By comparison with a standard spectrum, it is then possible to identify the original amino acid and obtain its quantification. The whole process is controlled by a computer which controls the different elements and ensures the acquisition of data as well as their processing.

Results

Thus, it was possible to obtain approximately 30 amino acids from the N-terminal ends of 5 monomers and an linker isolated by reversed-phase.

Details of PCR Amplification Protocols and Presentation of the Nucleotide and Polypeptide Sequences of the Globins of the Sub-Families A1, A2a, A2b, B2 and B1 and the Linker L1 of the Marine Polychaete *Arenicola marina*

The PCR amplifications of the 5 globins A1, A2a, A2b, B1 and B2, as well as of the linker L1, the nucleotide sequences of which are presented below, commenced with the design of specific degenerated primers (sense and antisense) of the sub-families A1, A2, B1 and B2. These primers, which allowed the amplification of the abovementioned five globins (A1, A2a, A2b, B1 and B2) then the cloning and sequencing of the corresponding PCR products, were designed from alignments of protein sequences of Annelida globins available from the data banks.

The complementary DNA matrices used for the PCR reactions were synthesized from messenger RNAs purified from total RNAs extracted from Arenicolas, due to the small size of the organisms and their intense growth rate reflecting significant levels of expression of the genes, including those involved in the synthesis of the haemoglobin. The complementary DNAs have thus been synthesized. These stages made use of commercial molecular biology kits produced by Ambion (purification of the RNAs), Amersham (purification of the mRNAs), Promega®, Invitrogene (cloning), Abgene (sequencing).

In a second phase, we developed the PCR reactions, in particular as regards the determination of the denaturation time, hybridization time and temperature and elongation time parameters. The $MgCl_2$ concentrations were also optimized.

Finally, in a last stage, 5' and 3' RACE PCR experiments were carried out so as to obtain the complete coding sequences. These stages used the Roche molecular biology kit.

The nucleotide sequences of the degenerated sense and antisense primers, the PCR parameters and the partial or complete coding sequences for each of the globins A2a, A2b, A1, B1 and B2, and for the linker L1 are presented below.

It is specified that the total blast databank analysis of these sequences produces values comprised between $2.10^{-3} < \text{Evaluate} < 5^{e-31}$.

Globin A2a

In order to obtain the nucleotide sequence SEQ ID NO: 1 encoding the globin A2a (SEQ ID NO: 2), the pair of primers (SEQ ID NO: 19; SEQ ID NO: 20) are used.

The PCR conditions are the following:

| | | |
|---|---|---|
| Time and initial temperature of denaturation: | 4 min at 95° C. | |
| Time and Temperature of denaturation: | 30 s at 95° C. | |
| Time and Temperature of hybridization: | 30 s at 56° C. | 35 cycles |
| Time and Temperature of elongation: | 40 s at 72° C. | |
| Time and Temperature of final elongation: | 10 min at 72° C. | |

PCR Reaction:
Per Reaction:
5-20 ng cDNA
100 ng sense primer
100 ng antisense primer
dNTP 200 μM final
$MgCl_2$ 2 mM final
Buffer PCR 1× final
1 unit Taq Polymerase
Qsf 25 μL $H_2O$ Globin A2b In order to obtain the nucleotide sequence SEQ ID NO: 3 encoding the globin A2b (SEQ ID NO: 4), the pair of primers (SEQ ID NO: 21; SEQ ID NO: 20) are used.

The PCR conditions are the following:

| | | |
|---|---|---|
| PCR: | 4 min at 95° C. | |
| | 30 s at 95° C. | |
| | 30 s at 52° C. | 35 cycles |
| | 40 s at 72° C. | |
| | 10 min at 72° C. | |

Globin A1

In order to obtain the nucleotide sequence SEQ ID NO: 5 encoding the globin A1 (SEQ ID NO: 6), the pair of primers (SEQ ID NO: 22; SEQ ID NO: 20) are used.

The PCR conditions are the following:

| PCR: | 4 min at 95° C. |  |
|---|---|---|
|  | 1 min at 95° C. |  |
|  | 1 min at 50° C. | } 35 cycles |
|  | 1 min 30 at 72° C. |  |
|  | 10 min at 72° C. |  |

Globin B2

In order to obtain the nucleotide sequence SEQ ID NO: 7 encoding the globin B2 (SEQ ID NO: 8), the pair of primers (SEQ ID NO: 23; SEQ ID NO: 20) are used.

The PCR conditions are the following:

| PCR: | 4 min at 95° C. |  |
|---|---|---|
|  | 30 s at 95° C. |  |
|  | 40 s at 52° C. | } 35 cycles |
|  | 30 s at 72° C. |  |
|  | 10 min at 72° C. |  |

Globin B1

In order to obtain the nucleotide sequence SEQ ID NO: 9 encoding the globin B1 (SEQ ID NO: 10), the pair of primers (SEQ ID NO: 24; SEQ ID NO: 20) are used.

The PCR conditions are the following:

| PCR: | 4 min at 95° C. |  |
|---|---|---|
|  | 30 s at 95° C. |  |
|  | 40 s at 52° C. | } 35 cycles |
|  | 30 s at 72° C. |  |
|  | 10 min at 72° C. |  |

Linker L1

In order to obtain the nucleotide sequence SEQ ID NO: 11 encoding the Linker L1 (SEQ ID NO: 12), the pair of primers (SEQ ID NO: 25; SEQ ID NO: 20) are used.

The PCR conditions are the following:

| PCR: | 4 min at 95° C. |  |
|---|---|---|
|  | 40 s at 95° C. |  |
|  | 1 min at 58° C. | } 35 cycles |
|  | 1 min at 72° C. |  |
|  | 10 min at 72° C. |  |

BIBLIOGRAPHICAL REFERENCES

Bunn, H. F. et Jandl, J. H. (1968) *Trans Assoc Am Physicians,* 81, 147,

Chang, T. M. S. (1957) *Hemoglobin Corpuscles*, McGill University,

Chang, T. M. S. (1964) *Science,* 146, 524-525,

Chang, T. M. S. (1971) *Biochem. Biophys. Res. Com.,* 44, 1531-1533,

Chang, T. M. S. (1997) *Blood substitutes: principals, methods, products and clinical trials*, Vol. I, Karger, Basel, Suisse, Chiancone, E., et al. (1972) Studies on erythrocruorin. II. Dissociation of earthworm erythrocruorin, *J Mol Biol,* 70(1): 73-84, Clark, L. C. J. et Gollan, F. (1966) *Science,* 152, 1755, De Haas, F.; Boisset, N.; Taveau, J. C.; Lambert, O.; Vinogradov, S. N. and Lamy, J. N. (1996) *Biophys. J,* 70, 1973-1984, De Haas, F.; Taveau, J.-C.; Boisset, N.; Lambert, O.; Vinogradov, S. N. and Lamy, J. N. (1996) *J. Mol. Biol.,* 255, 140-153, De Haas, F.; Zal, F.; Lallier, F. H.; Toulmond, A. and Lamy, J. N. (1996) Proteins-structure fonction and genetics, 3, 241-256, De Haas, F.; Zal, F.; You, V.; Lallier, F. H.; Toulmond, A. and Lamy, J. N. (1996) *J. Mol. Biol.,* 264, 111-120, Dickerson, R. E. and Geis, I. (1983) *Hemoglobin: Structure, function, evolution, and pathology*, Benjamin/Cummings, Menlo Park, Calif., Geyer, R. P.; Monroe, R. G. and Taylor, K. (1968) *Survival of rats totally perfused with a fluorocarbon-detergent preparation*, J. C. Norman, J. Folkman, W. G. Hardisson, L. E. Rudolf and F. J. Veith (Eds), 85-96, Appleton Century Crofts, New York, Goodin, T. H.; Grossbard, E. B.; Kaufman, R. J.; Richard, T. J.; Kolata, R. J.; Allen, J. S. and Layton, T. E. (1994), *Crit Care Med,* 22, 680-689, Hirsch, R. E.; Jelicks, L. A.; Wittenberg, B. A.; Kaul, D. K.; Shear, H. L. and Harrington, J. P. (1997) Artificial Cells, Blood Substitutes & Immobilization Biotechnology, 25, 429-444, Jia, L.; Bonaventura, C.; Bonaventura, J. and Stamler, J. S. (1996) *Nature,* 380, 221-226, Kapp, O. H. and Crewe, A. V. (1984) *Biochim. Biophys. Acta* 789, 294-301, Kapp, O. H., et al. (1984) The reassociation of *Lumbricus terrestris* hemoglobin dissociated at alkaline pH, *J Biol Chem,* 259(1): 628-39, Krebs, A., et al. (1996) Molecular shape, dissociation, and oxygen binding of the dodecamer subunit of *Lumbricus terrestris* hemoglobin, *J Biol Chem,* 271(31): 18695-704, Lamy, J. N.; Green, B. N.; Toulmond, A., Wall, J. S.; Weber, R. E. and Vinogradov, S. N. (1996), *Chem. Rev.* 96, 3113-3124

Levin, O. (1963) *J. Mol. Biol.,* 6, 95-101,

Mainwaring, M. G., et al. (1986) The dissociation of the extracellular hemoglobin of *Lumbricus terrestris* at acid pH and its reassociation at neutral pH. A new model of its quaternary structure, *J Biol Chem,* 261(23): 10899-908, Mitsuno, T. and Naito, R. (1979) *Perfluorochemical Blood Substitutes*, Excerpta Medica, Amsterdam, Mitsuno, T. and Ohyanagi, H. (1985) *Present status of clinical studies of fluosol-DA (20%) in Japan*, K. K. Tremper (Ed), 169-184, Little Brown & Co, Boston, Naito, R. and Y. K. (1978) *An improved perfluorodecalin emulsion. In Blood Substitutes and Plasma Expanders*, G. A. Jamieson and T. J. Greenwalt (Eds), 81, Alan R. Liss Inc., New York, Nho, K.; Glower, D.; Bredehoeft, S.; Shankar, H.; Shorr, R. and Abuchowski, A. (1992) Biomaterials, Artificial Cells and Immobilization Biotechnology, An International Journal, 20, 511-524, Payne, J. W. (1973) *Biochem J.* 135, 866-873, Polidori, G., et al. (1984) The dissociation of the extracellular hemoglobin of *Tubifex tubifex* at extremes of pH and its reassociation upon return to neutrality, *Arch Biochem Biophys,* 233(2): 800-14, Reiss, J. G. (1991) *Vox Sang,* 61, 225-239, Reiss, J. G., (1994) Artificial Cells, Blood substitutes & Immobilization Biotechnology, An International Journal 22, 945-1511, Roche, J. (1965) *Electron microscope studies on high molecular weight erythrocruorins (invertebrate hemoglobins) and chlorocruorins of annelids*, D. A. Munday (Ed), 62-80, Pergamon Press, Oxford, Roche, J.; Bessis, M. and Thiery, J. P. (1960) *Biochim. Biophys. Acta*, 41, 182-184, Roche, J.; Bessis, M. T. and Thiery, J. P. (1960) *C. R. Soc. Biol.* 154, 73-80, Sharma, P. K., et al. (1996) The role of the dodecamer subunit in the dissociation and reassembly of the hexagonal bilayer structure of *Lumbricus terrestris* hemoglobin, *J Biol Chem*, 271(15): 8754-62, Sloviter, H. and Kamimoto, T. (1967) *Nature*, 216, 458, Terwilliger, N. B. (1992) *Molecular Structure of the extracellular heme proteins*, Vol. 13, C. P. Mangum (Ed), 193-229, Springer-Verlag, Berlin, Van Bruggen, E. F. J. and Weber, R. E. (1974) *Biochim. Biophys. Acta*, 359, 210-212, Vinogradov, S. N., et al. (1991) A dodecamer of globin chains is the principal functional subunit of the extracellular hemoglobin of *Lumbricus terrestris*, *J Biol Chem*, 266(20): 13091-6, Vinogradov, S. N., Shlom J. M. and Doyle, M. (1979) Dissociation of the extracellular hemoglobin of *Arenicola cristata*. *Comp. Biochem. Physiol.*, 65B: 145-150, Vinogradov, S. N. (1985) The structure of invertebrate extracellular hemoglobins (erythrocruorins and chlorocruorins), *Comp Biochem Physiol B*, 82(1): 1-15, Zal, F.; Green, B. N.; Lallier, F. H.; Vinogradov, S. N. and Toulmond, A. (1997) *Eur. J. Biochem.*, 243, 85-92.

The invention claimed is:

1. A method of obtaining protein chains from the extracellular hemoglobin molecule of *Arenicola marina*,
   the method comprising bringing together a sample of the extracellular hemoglobin molecule of *Arenicola marina* and a dissociation buffer for a time sufficient to separate the protein chains from each other, wherein the dissociation buffer comprises at least one dissociating agent, and optionally, a reducing agent, and the protein chains comprise an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

2. The method according to claim 1, wherein the dissociation buffer comprises about 0.05 M to 0.1 M Trisma (tris(hydroxymethyl)aminomethane) and about 0 to 10 mM EDTA, and has a pH of about 5 to 12.

3. The method according to claim 1, wherein the dissociation buffer comprises a reducing agent, and the protein chains are obtained from the reduction of four sub-units of the extracellular hemoglobin molecule.

4. A method of preparing primer pairs capable of hybridizing to a nucleic acid encoding the protein chains obtained according to the method as defined in claim 1, the method comprising:
   isolating each of the protein chains from the hemoglobin molecule,
   microsequencing each of the isolated protein chains to obtain a microsequence corresponding to each of the protein chain sequences, each microsequence comprising 5 to 20 amino acids, and
   determining degenerate primer pairs from the microsequences, wherein the degenerate primer pairs are capable of hybridizing to a nucleic acid encoding the protein chains.

5. Primer pairs for preparing a nucleic acid encoding the protein chains obtained according to the method as defined in claim 1, the primer pairs selected from the list consisting of:

```
a) Sense primer:      GAR TGY GGN      (SEQ ID NO: 21)
                      CCN TTR CAR Antisense primer:  CTC CTC TCC      (SEQ ID NO: 22)
                      TCT CCT CTT
                      CCT b) Sense primer:      TGY GGN ATH      (SEQ ID NO: 23)
                      CTN CAR CG Antisense primer:  CTC CTC TCC      (SEQ ID NO: 22)
                      TCT CCT CTT
                      CCT c) Sense primer:      AAR GTI AAR      (SEQ ID NO: 24)
                      CAN AAC TGG Antisense primer:  CTC CTC TCC      (SEQ ID NO: 22)
                      TCT CCT CTT
                      CCT d) Sense primer:      TGY TGY AGY      (SEQ ID NO: 25)
                      ATH GAR GAY
                      CG Antisense primer:  CTC CTC TCC      (SEQ ID NO: 22)
                      TCT CCT CTT
                      CCT e) Sense primer:      AAR GTN ATH      (SEQ ID NO: 26)
                      TTY GGN AGR
                      GA Antisense primer:  CTC CTC TCC      (SEQ ID NO: 22)
                      TCT CCT CTT
                      CCT f) Sense primer:      GAR CAY CAR      (SEQ ID NO: 27)
                      TGY GGN GGN
                      GA Antisense primer:  CTC CTC TCC      (SEQ ID NO: 22)
                      TCT CCT CTT
                      CCT
``` wherein,
R represents A or G,
Y represents C or T,
N represents A, G, C or T,
I represents inosine, and
H represents A, C or T.

6. A method for preparing a nucleotide sequence encoding a protein chain of the extracellular hemoglobin molecule of *Arenicola marina*, utilizing at least one of the primer pairs of claim 5, the method comprising a polymerase chain reaction (PCR) of at least 30 cycles of the following steps:

denaturing cDNA encoding one of the protein chains so as to denature any secondary structures and RNA residuals, the cDNA being obtained from mRNA, to obtain strands of denatured monocatenary cDNA, hybridizing the primer pair to the strands of denatured monocatenary cDNA at an appropriate temperature, to obtain hybridized primers, and synthesizing a complementary strand of the cDNA using a polymerase at an appropriate temperature.

7. A protein encoded by a nucleotide sequence obtained according to the method as defined in claim 6.

8. The protein according to claim 7, wherein the protein comprises:
the sequence SEQ ID NO: 2.

9. The protein according to claim 7, wherein the protein comprises:
the sequence SEQ ID NO: 4.

10. The protein according to claim 7, wherein the protein comprises:
the sequence SEQ ID NO: 6.

11. The protein according to claim 7, wherein the protein comprises:
the sequence SEQ ID NO: 8.

12. The protein according to claim 7, wherein the protein comprises:
the sequence SEQ ID NO: 10.

13. The protein according to claim 7, wherein the protein comprises:
the sequence SEQ ID NO: 12.

14. A nucleotide sequence obtained according to the method as defined in claim 6.

15. A nucleotide sequence encoding a protein as defined in claim 7.

16. The nucleotide sequence according to claim 15, comprising
the nucleotide sequence SEQ ID NO: 1 encoding a protein represented by SEQ ID NO: 2.

17. The nucleotide sequence according to claim 15, comprising
the nucleotide sequence SEQ ID NO: 3 encoding a protein represented by SEQ ID NO: 4.

18. The nucleotide sequence according to claim 15, comprising
the nucleotide sequence SEQ ID NO: 5 encoding a protein represented by SEQ ID NO: 6.

19. The nucleotide sequence according to claim 15, comprising
the nucleotide sequence SEQ ID NO: 7 encoding a protein represented by SEQ ID NO: 8.

20. The nucleotide sequence according to claim 15, comprising
the nucleotide sequence SEQ ID NO: 9 encoding a protein represented by SEQ ID NO: 10.

21. The nucleotide sequence according to claim 15, comprising
the nucleotide sequence SEQ ID NO: 11 encoding a protein represented by SEQ ID NO: 12.

22. A method for preparing nucleotide sequences encoding a protein chain of extracellular hemoglobin molecule of *Arenicola marina*, the method comprising the following steps:

bringing together a sample of the hemoglobin molecule and a dissociation buffer for a time sufficient to separate the protein chains from each other, wherein the dissociation buffer comprises at least one dissociating agent and a reducing agent, dissociating and reducing the hemoglobin molecule to obtain the protein chains, isolating each of the protein chains, microsequencing each of the isolated protein chains to obtain a microsequence corresponding to each of the protein chain sequences, each microsequence comprising 5 to 20 amino acids, determining degenerate primer pairs from the microsequence, wherein the degenerate primer pairs are capable of hybridizing to nucleic acid encoding the protein chains, preparing nucleotide sequences encoding the protein chains, utilizing the degenerate primer pairs, by a polymerase chain reaction (PCR) comprising an initial step of denaturing for approximately 10 seconds to approximately 5 minutes at a temperature between approximately 90° C. and approximately 110° C., followed by 30 to 40 cycles of the following steps:

denaturing for approximately 10 seconds to approximately 5 minutes at a temperature between approximately 90° C. and approximately 110° C., hybridizing for approximately 20 seconds to approximately 2 minutes at a temperature between approximately 50° C. and approximately 56° C., elongating for approximately 20 seconds to approximately 90 seconds at a temperature between approximately 70° C. and approximately 75° C., and a further final step comprising elongation of approximately 5 minutes to approximately 15 minutes at a temperature between approximately 70° C. and approximately 75° C., wherein the protein chains comprise an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

23. An isolated protein comprising an amino acid sequence of SEQ ID NO: 2.

24. An isolated protein encoded by a nucleic acid comprising a nucleotide sequence of SEQ ID NO: 1.

25. The method according to claim 1, wherein the dissociation buffer comprises dithiothreitol (DTT), tris(2-carboxyethyl)phosphine hydrochloride (TCEP), beta-mercaptoethanol, or any combination thereof.

26. The method according to claim 2, wherein the dissociation buffer has a pH of about 7.5 to 12.

27. The method according to claim 22, wherein the dissociation buffer comprises dithiothreitol (DTT), tris(2-carboxyethyl)phosphine hydrochloride (TCEP), beta-mercaptoethanol, or any combination thereof.

* * * * *

SEQUENCE LISTING

```
<160> NUMBER OF SEQ ID NOS: 31

<210> SEQ ID NO 1
<211> LENGTH: 474
<212> TYPE: DNA
<213> ORGANISM: Arenicola marina
<220> FEATURE:
<221> NAME/KEY: CDS
<222> LOCATION: (1)..(474)
<223> OTHER INFORMATION:

<400> SEQUENCE: 1 atg aag tcc ttg gtg gtt ctg ttc gcc ctg gtg gcc atg gtg gct gca      48
Met Lys Ser Leu Val Val Leu Phe Ala Leu Val Ala Met Val Ala Ala
1               5                   10                  15 gag tgc ggc ccc atg cag cgc ctc ctg gtc aag acc cag tgg aac aag      96
Glu Cys Gly Pro Met Gln Arg Leu Leu Val Lys Thr Gln Trp Asn Lys
            20                  25                  30 gtg tac ggc acc agc aag gtc agg gac gag gcc gga cac gtc ctc tgg     144
Val Tyr Gly Thr Ser Lys Val Arg Asp Glu Ala Gly His Val Leu Trp
        35                  40                  45 aag gct att ttc gcc cag gat ccc gag acc cgg gct ctc ttc aag aga     192
Lys Ala Ile Phe Ala Gln Asp Pro Glu Thr Arg Ala Leu Phe Lys Arg
    50                  55                  60 gtc aac ggt gac gac atc tac tct ccc gag ttc atg gct cac agc gcc     240
Val Asn Gly Asp Asp Ile Tyr Ser Pro Glu Phe Met Ala His Ser Ala
65                  70                  75                  80 cgt gtc ttg ggt ggc ctt gac att gcc atc tcc ctc ctc gac aac cag     288
Arg Val Leu Gly Gly Leu Asp Ile Ala Ile Ser Leu Leu Asp Asn Gln
                85                  90                  95 gct gac ctt gac gtc gcc ctg gct cac ctt cac gtg cag cac gta gaa     336
Ala Asp Leu Asp Val Ala Leu Ala His Leu His Val Gln His Val Glu
            100                 105                 110 agg cac atc cca acc cgc tac ttc gat ctg ttc aag aac gcc ctg atg     384
Arg His Ile Pro Thr Arg Tyr Phe Asp Leu Phe Lys Asn Ala Leu Met
        115                 120                 125 gag tat gcc ccc agc gcc ctg gga cgc tgc ttc gat aag acc gcc tgg     432
Glu Tyr Ala Pro Ser Ala Leu Gly Arg Cys Phe Asp Lys Thr Ala Trp
    130                 135                 140 agc tcg tgc ttt gac gtc atc gcc aac ggc atc aag gaa tag             474
Ser Ser Cys Phe Asp Val Ile Ala Asn Gly Ile Lys Glu
145                 150                 155
```

-continued

<210> SEQ ID NO 2
<211> LENGTH: 157
<212> TYPE: PRT
<213> ORGANISM: Arenicola marina

<400> SEQUENCE: 2

Met Lys Ser Leu Val Val Leu Phe Ala Leu Val Ala Met Val Ala Ala
1               5                   10                  15

Glu Cys Gly Pro Met Gln Arg Leu Leu Val Lys Thr Gln Trp Asn Lys
            20                  25                  30

Val Tyr Gly Thr Ser Lys Val Arg Asp Glu Ala Gly His Val Leu Trp
        35                  40                  45

Lys Ala Ile Phe Ala Gln Asp Pro Glu Thr Arg Ala Leu Phe Lys Arg
    50                  55                  60

Val Asn Gly Asp Asp Ile Tyr Ser Pro Glu Phe Met Ala His Ser Ala
65                  70                  75                  80

Arg Val Leu Gly Gly Leu Asp Ile Ala Ile Ser Leu Leu Asp Asn Gln
                85                  90                  95

Ala Asp Leu Asp Val Ala Leu Ala His Leu His Val Gln His Val Glu
            100                 105                 110

Arg His Ile Pro Thr Arg Tyr Phe Asp Leu Phe Lys Asn Ala Leu Met
        115                 120                 125

Glu Tyr Ala Pro Ser Ala Leu Gly Arg Cys Phe Asp Lys Thr Ala Trp
    130                 135                 140

Ser Ser Cys Phe Asp Val Ile Ala Asn Gly Ile Lys Glu
145                 150                 155

<210> SEQ ID NO 3
<211> LENGTH: 477
<212> TYPE: DNA
<213> ORGANISM: Arenicola marina
<220> FEATURE:
<221> NAME/KEY: CDS
<222> LOCATION: (1)..(477)
<223> OTHER INFORMATION:

<400> SEQUENCE: 3 atg aag ttc ttg gtg gtt ctg ttc gcc ctg gtg gcc atg gtc gct gct      48
Met Lys Phe Leu Val Val Leu Phe Ala Leu Val Ala Met Val Ala Ala
1               5                   10                  15 gat tgt ggc ccc atg cag cgc ctc ctg gtc aag gcc cag tgg aac aag      96
Asp Cys Gly Pro Met Gln Arg Leu Leu Val Lys Ala Gln Trp Asn Lys
            20                  25                  30 gtg tac ggc acc agc aag gtc agg gac gac gcc gga cac gtc ctc tgg     144
Val Tyr Gly Thr Ser Lys Val Arg Asp Asp Ala Gly His Val Leu Trp
        35                  40                  45 aag gct atc ttc aac cag gat ggt gag acc cgc gcc ctc ttc aac aga     192
Lys Ala Ile Phe Asn Gln Asp Gly Glu Thr Arg Ala Leu Phe Asn Arg
    50                  55                  60 gtg cac ggt gac gac atc tac tct ccc gag ttc atg gct cac agc gcc     240
Val His Gly Asp Asp Ile Tyr Ser Pro Glu Phe Met Ala His Ser Ala
65                  70                  75                  80 cgt gtc ttg ggt ggc ctt gac att gcc atc tcc ctc ctc gac aac cag     288
Arg Val Leu Gly Gly Leu Asp Ile Ala Ile Ser Leu Leu Asp Asn Gln
                85                  90                  95 gct gag ctt gac gct gtc ctg gct cac ctc aag gag cag cac att gag     336
Ala Glu Leu Asp Ala Val Leu Ala His Leu Lys Glu Gln His Ile Glu
            100                 105                 110 agg ggg atc cca gac cgt tac ttc gac ctg ttc aag aac gcc ctg atg     384
Arg Gly Ile Pro Asp Arg Tyr Phe Asp Leu Phe Lys Asn Ala Leu Met

```
                115                 120                 125
gag ttt gcc ccc agc gcc ttg gga cgc tgc ttc ata aag gac gct tgg       432
Glu Phe Ala Pro Ser Ala Leu Gly Arg Cys Phe Ile Lys Asp Ala Trp
    130                 135                 140 agc tca tgc ttt gac gtc att gcc aac ggc atc aag gga cag taa           477
Ser Ser Cys Phe Asp Val Ile Ala Asn Gly Ile Lys Gly Gln
145                 150                 155

<210> SEQ ID NO 4
<211> LENGTH: 158
<212> TYPE: PRT
<213> ORGANISM: Arenicola marina

<400> SEQUENCE: 4

Met Lys Phe Leu Val Val Leu Phe Ala Leu Val Ala Met Val Ala Ala
1               5                   10                  15

Asp Cys Gly Pro Met Gln Arg Leu Leu Val Lys Ala Gln Trp Asn Lys
            20                  25                  30

Val Tyr Gly Thr Ser Lys Val Arg Asp Asp Ala Gly His Val Leu Trp
        35                  40                  45

Lys Ala Ile Phe Asn Gln Asp Gly Glu Thr Arg Ala Leu Phe Asn Arg
    50                  55                  60

Val His Gly Asp Asp Ile Tyr Ser Pro Glu Phe Met Ala His Ser Ala
65                  70                  75                  80

Arg Val Leu Gly Gly Leu Asp Ile Ala Ile Ser Leu Leu Asp Asn Gln
                85                  90                  95

Ala Glu Leu Asp Ala Val Leu Ala His Leu Lys Glu Gln His Ile Glu
            100                 105                 110

Arg Gly Ile Pro Asp Arg Tyr Phe Asp Leu Phe Lys Asn Ala Leu Met
        115                 120                 125

Glu Phe Ala Pro Ser Ala Leu Gly Arg Cys Phe Ile Lys Asp Ala Trp
    130                 135                 140

Ser Ser Cys Phe Asp Val Ile Ala Asn Gly Ile Lys Gly Gln
145                 150                 155

<210> SEQ ID NO 5
<211> LENGTH: 474
<212> TYPE: DNA
<213> ORGANISM: Arenicola marina
<220> FEATURE:
<221> NAME/KEY: CDS
<222> LOCATION: (1)..(474)
<223> OTHER INFORMATION:

<400> SEQUENCE: 5 atg aag gtc ctg atc gta ctg atg gcc tgc ttg gcc tac gtc gcc gcc       48
Met Lys Val Leu Ile Val Leu Met Ala Cys Leu Ala Tyr Val Ala Ala
1               5                   10                  15 gac tgc gga cct ctg cag agg ctg aag gtg aag cat cag tgg gtg cag       96
Asp Cys Gly Pro Leu Gln Arg Leu Lys Val Lys His Gln Trp Val Gln
            20                  25                  30 gtg tac agc ggc cat ggt tac gag cgt gag gcg ttc ggc aga gag gtc      144
Val Tyr Ser Gly His Gly Tyr Glu Arg Glu Ala Phe Gly Arg Glu Val
        35                  40                  45 ttc ctc gag atg tac aac cag gca ccc aag gcc aag gac ctc ttc acc      192
Phe Leu Glu Met Tyr Asn Gln Ala Pro Lys Ala Lys Asp Leu Phe Thr
    50                  55                  60 agg gtc agg ggc gag aac gtc ttc tcc ccc gag ttc gga gcc cac atg      240
Arg Val Arg Gly Glu Asn Val Phe Ser Pro Glu Phe Gly Ala His Met
65                  70                  75                  80
```

```
gtc cgt gtg ctc gga gga ctc gac atg tgc atc gct ctg ctg tcc gat       288
Val Arg Val Leu Gly Gly Leu Asp Met Cys Ile Ala Leu Leu Ser Asp
                85                  90                  95 gac acc gtc ctc aac gcc cag ctt gct cac ctc agc acg cag cac aag       336
Asp Thr Val Leu Asn Ala Gln Leu Ala His Leu Ser Thr Gln His Lys
        100                 105                 110 gac cgt gga atc ccc aac gag tac ttc gat gtg atg aag gtc gcc ctc       384
Asp Arg Gly Ile Pro Asn Glu Tyr Phe Asp Val Met Lys Val Ala Leu
    115                 120                 125 atg aag gtc gtc ccc ggc cac gtt tca cac ttc gac ttc gat gcc tgg       432
Met Lys Val Val Pro Gly His Val Ser His Phe Asp Phe Asp Ala Trp
130                 135                 140 tct gcc tgc tat gac gtc atc gcc aac ggc atc aag cac taa               474
Ser Ala Cys Tyr Asp Val Ile Ala Asn Gly Ile Lys His
145                 150                 155

<210> SEQ ID NO 6
<211> LENGTH: 157
<212> TYPE: PRT
<213> ORGANISM: Arenicola marina

<400> SEQUENCE: 6

Met Lys Val Leu Ile Val Leu Met Ala Cys Leu Ala Tyr Val Ala Ala
1               5                   10                  15

Asp Cys Gly Pro Leu Gln Arg Leu Lys Val Lys His Gln Trp Val Gln
            20                  25                  30

Val Tyr Ser Gly His Gly Tyr Glu Arg Glu Ala Phe Gly Arg Glu Val
        35                  40                  45

Phe Leu Glu Met Tyr Asn Gln Ala Pro Lys Ala Lys Asp Leu Phe Thr
    50                  55                  60

Arg Val Arg Gly Glu Asn Val Phe Ser Pro Glu Phe Gly Ala His Met
65                  70                  75                  80

Val Arg Val Leu Gly Gly Leu Asp Met Cys Ile Ala Leu Leu Ser Asp
                85                  90                  95

Asp Thr Val Leu Asn Ala Gln Leu Ala His Leu Ser Thr Gln His Lys
            100                 105                 110

Asp Arg Gly Ile Pro Asn Glu Tyr Phe Asp Val Met Lys Val Ala Leu
        115                 120                 125

Met Lys Val Val Pro Gly His Val Ser His Phe Asp Phe Asp Ala Trp
    130                 135                 140

Ser Ala Cys Tyr Asp Val Ile Ala Asn Gly Ile Lys His
145                 150                 155

<210> SEQ ID NO 7
<211> LENGTH: 498
<212> TYPE: DNA
<213> ORGANISM: Arenicola marina
<220> FEATURE:
<221> NAME/KEY: CDS
<222> LOCATION: (1)..(498)
<223> OTHER INFORMATION:

<400> SEQUENCE: 7 atg ctt cgt ttc gta gca ctc ttg gct ctg gtc ggc ctg gcc gtc tgt        48
Met Leu Arg Phe Val Ala Leu Leu Ala Leu Val Gly Leu Ala Val Cys
1               5                   10                  15 gac gac tgt tgt acc acc gag gac cgc aag gag gtc cag acg ctg tgg        96
Asp Asp Cys Cys Thr Thr Glu Asp Arg Lys Glu Val Gln Thr Leu Trp
            20                  25                  30
```

```
agt gag atc tgg agt gcc cag ttc act ggt cgc cgt gtc cag gtt gcc      144
Ser Glu Ile Trp Ser Ala Gln Phe Thr Gly Arg Arg Val Gln Val Ala
         35                  40                  45 cag gct gtg ttc gag gac ctc ttc cgc cgc gac ccc gag tcc aag aac      192
Gln Ala Val Phe Glu Asp Leu Phe Arg Arg Asp Pro Glu Ser Lys Asn
 50                  55                  60 ctg ttc aag cgc gtc aat gtt gac gac atg aac agc ccc gaa ttc cac      240
Leu Phe Lys Arg Val Asn Val Asp Asp Met Asn Ser Pro Glu Phe His
 65                  70                  75                  80 gct cac tgc atc cgt gtt gtc aac ggt ctt gac acc gtg atc ggt ctc      288
Ala His Cys Ile Arg Val Val Asn Gly Leu Asp Thr Val Ile Gly Leu
                 85                  90                  95 ctt gac gac ccc gac acc ctg aag tcc cag ctc gag cac ttg gcc cag      336
Leu Asp Asp Pro Asp Thr Leu Lys Ser Gln Leu Glu His Leu Ala Gln
            100                 105                 110 cag cac aag gag cgt gat ggc atc cac aag acc cac ttc gac gag atg      384
Gln His Lys Glu Arg Asp Gly Ile His Lys Thr His Phe Asp Glu Met
        115                 120                 125 tcc cac gcc ttc ggc gcc gtc atg ccc cag gtc agc agc tgc ttc aac      432
Ser His Ala Phe Gly Ala Val Met Pro Gln Val Ser Ser Cys Phe Asn
130                 135                 140 ccc gat gcc tgg aac cgt tgc ttc ggc tcc atc gct acc aag att gct      480
Pro Asp Ala Trp Asn Arg Cys Phe Gly Ser Ile Ala Thr Lys Ile Ala
145                 150                 155                 160 tcc ctc ctc gag gat taa                                              498
Ser Leu Leu Glu Asp
            165

<210> SEQ ID NO 8
<211> LENGTH: 165
<212> TYPE: PRT
<213> ORGANISM: Arenicola marina

<400> SEQUENCE: 8

Met Leu Arg Phe Val Ala Leu Leu Ala Leu Val Gly Leu Ala Val Cys
 1               5                  10                  15

Asp Asp Cys Cys Thr Thr Glu Asp Arg Lys Glu Val Gln Thr Leu Trp
            20                  25                  30

Ser Glu Ile Trp Ser Ala Gln Phe Thr Gly Arg Arg Val Gln Val Ala
         35                  40                  45

Gln Ala Val Phe Glu Asp Leu Phe Arg Arg Asp Pro Glu Ser Lys Asn
 50                  55                  60

Leu Phe Lys Arg Val Asn Val Asp Asp Met Asn Ser Pro Glu Phe His
 65                  70                  75                  80

Ala His Cys Ile Arg Val Val Asn Gly Leu Asp Thr Val Ile Gly Leu
                 85                  90                  95

Leu Asp Asp Pro Asp Thr Leu Lys Ser Gln Leu Glu His Leu Ala Gln
            100                 105                 110

Gln His Lys Glu Arg Asp Gly Ile His Lys Thr His Phe Asp Glu Met
        115                 120                 125

Ser His Ala Phe Gly Ala Val Met Pro Gln Val Ser Ser Cys Phe Asn
130                 135                 140

Pro Asp Ala Trp Asn Arg Cys Phe Gly Ser Ile Ala Thr Lys Ile Ala
145                 150                 155                 160

Ser Leu Leu Glu Asp
            165

<210> SEQ ID NO 9
```

```
<211> LENGTH: 498
<212> TYPE: DNA
<213> ORGANISM: Arenicola marina
<220> FEATURE:
<221> NAME/KEY: CDS
<222> LOCATION: (1)..(498)
<223> OTHER INFORMATION:

<400> SEQUENCE: 9 atg atg tcc gtc gtg ttc ctc ctc ggc ctt gtg gcc tac gcc tcc gcc    48
Met Met Ser Val Val Phe Leu Leu Gly Leu Val Ala Tyr Ala Ser Ala
 1               5                  10                  15 tcc agc tgc tgc tcc tat gga gac cag cag aag gtc aag gcc cag tgg    96
Ser Ser Cys Cys Ser Tyr Gly Asp Gln Gln Lys Val Lys Ala Gln Trp
             20                  25                  30 aac agc ctc tgg aac acc cct gac tcc tcc aca tcc aag atc atc ttc   144
Asn Ser Leu Trp Asn Thr Pro Asp Ser Ser Thr Ser Lys Ile Ile Phe
         35                  40                  45 gga aag gaa gtc ttc gca cgc ttc ttc gag gtt gac ccc gag agc aag   192
Gly Lys Glu Val Phe Ala Arg Phe Phe Glu Val Asp Pro Glu Ser Lys
     50                  55                  60 agc ctg ttc ggt cgc gtc aag gtt gaa gac ccc gac agc ccc gag ttc   240
Ser Leu Phe Gly Arg Val Lys Val Glu Asp Pro Asp Ser Pro Glu Phe
 65                  70                  75                  80 gcc gga cac gtg atc cgt gtt ttg acc ggt ctg gat ttg atc atc aac   288
Ala Gly His Val Ile Arg Val Leu Thr Gly Leu Asp Leu Ile Ile Asn
                 85                  90                  95 ttg atg ggt gac gat gcc atg gat gcc gag ctg gcc cac ctt aac acc   336
Leu Met Gly Asp Asp Ala Met Asp Ala Glu Leu Ala His Leu Asn Thr
            100                 105                 110 cag cat ttg gcc aga gag gga atc acc gga acc cac ttc acc gag atg   384
Gln His Leu Ala Arg Glu Gly Ile Thr Gly Thr His Phe Thr Glu Met
        115                 120                 125 ttc aag gtc ctg gat gga tcc ctc cgc cag gtt ctc gag gag tac gat   432
Phe Lys Val Leu Asp Gly Ser Leu Arg Gln Val Leu Glu Glu Tyr Asp
    130                 135                 140 tcc ctg tcc tgg agg tac tgc ttc cgt ggt ctg ggc gcc gcc ctc agg   480
Ser Leu Ser Trp Arg Tyr Cys Phe Arg Gly Leu Gly Ala Ala Leu Arg
145                 150                 155                 160 gat ggt ctc ccc gca taa                                            498
Asp Gly Leu Pro Ala
                165

<210> SEQ ID NO 10
<211> LENGTH: 165
<212> TYPE: PRT
<213> ORGANISM: Arenicola marina

<400> SEQUENCE: 10

Met Met Ser Val Val Phe Leu Leu Gly Leu Val Ala Tyr Ala Ser Ala
 1               5                  10                  15

Ser Ser Cys Cys Ser Tyr Gly Asp Gln Gln Lys Val Lys Ala Gln Trp
             20                  25                  30

Asn Ser Leu Trp Asn Thr Pro Asp Ser Ser Thr Ser Lys Ile Ile Phe
         35                  40                  45

Gly Lys Glu Val Phe Ala Arg Phe Phe Glu Val Asp Pro Glu Ser Lys
     50                  55                  60

Ser Leu Phe Gly Arg Val Lys Val Glu Asp Pro Asp Ser Pro Glu Phe
 65                  70                  75                  80

Ala Gly His Val Ile Arg Val Leu Thr Gly Leu Asp Leu Ile Ile Asn
                 85                  90                  95
```

```
Leu Met Gly Asp Asp Ala Met Asp Ala Glu Leu Ala His Leu Asn Thr
            100                 105                 110

Gln His Leu Ala Arg Glu Gly Ile Thr Gly Thr His Phe Thr Glu Met
        115                 120                 125

Phe Lys Val Leu Asp Gly Ser Leu Arg Gln Val Leu Glu Glu Tyr Asp
130                 135                 140

Ser Leu Ser Trp Arg Tyr Cys Phe Arg Gly Leu Gly Ala Ala Leu Arg
145                 150                 155                 160

Asp Gly Leu Pro Ala
            165

<210> SEQ ID NO 11
<211> LENGTH: 771
<212> TYPE: DNA
<213> ORGANISM: Arenicola marina
<220> FEATURE:
<221> NAME/KEY: CDS
<222> LOCATION: (1)..(771)
<223> OTHER INFORMATION:

<400> SEQUENCE: 11
```

| | | |
|---|---|---|
| atg aag agc tac gtg ctc gtg tgc tgc ctc gtg gtg ggg gcc gtg gcc<br>Met Lys Ser Tyr Val Leu Val Cys Cys Leu Val Val Gly Ala Val Ala<br>1               5                   10                  15 | 48 |
| tac ccc cac gag gtg atg cac cat gcc gtt ggc gca aac cga atg tgc<br>Tyr Pro His Glu Val Met His His Ala Val Gly Ala Asn Arg Met Cys<br>            20                  25                  30 | 96 |
| aag tgt gat gcc ccg gca ggg aac gcc gaa acc tcc gcc gac aga gag<br>Lys Cys Asp Ala Pro Ala Gly Asn Ala Glu Thr Ser Ala Asp Arg Glu<br>        35                  40                  45 | 144 |
| cag agt cac act ctc gat gag ttg acc cat cag ttg cac atg ctg cag<br>Gln Ser His Thr Leu Asp Glu Leu Thr His Gln Leu His Met Leu Gln<br>    50                  55                  60 | 192 |
| caa gcc tac gac acc ggc atg ggt cgt gtc gat gac gtg atg gag gac<br>Gln Ala Tyr Asp Thr Gly Met Gly Arg Val Asp Asp Val Met Glu Asp<br>65                  70                  75                  80 | 240 |
| atg gac gac ctg tcc cac agg atc gcc gac cac gag aag gaa cac tgt<br>Met Asp Asp Leu Ser His Arg Ile Ala Asp His Glu Lys Glu His Cys<br>                85                  90                  95 | 288 |
| aag aag tat aga gag ttc cag tgc ggt ggt gac cat cca aag tgc atc<br>Lys Lys Tyr Arg Glu Phe Gln Cys Gly Gly Asp His Pro Lys Cys Ile<br>            100                 105                 110 | 336 |
| tcg aac ctc ctc gtc tgc gac ggt gac aac gac tgt gac aat gga gct<br>Ser Asn Leu Leu Val Cys Asp Gly Asp Asn Asp Cys Asp Asn Gly Ala<br>        115                 120                 125 | 384 |
| gat gag gct cgt tgt gat gtg ctc acc gag gct ggt agt agt tgg act<br>Asp Glu Ala Arg Cys Asp Val Leu Thr Glu Ala Gly Ser Ser Trp Thr<br>    130                 135                 140 | 432 |
| ggt act gtg gtc tac gat cac tgc acc aag cgt cgc cca gag acc atg<br>Gly Thr Val Val Tyr Asp His Cys Thr Lys Arg Arg Pro Glu Thr Met<br>145                 150                 155                 160 | 480 |
| aag ctc agc atc aag agc gtg gat acc gta ccc ttc ttc acc acc cac<br>Lys Leu Ser Ile Lys Ser Val Asp Thr Val Pro Phe Phe Thr Thr His<br>                165                 170                 175 | 528 |
| ccc aag gtc cgc ggt acc gtg ctt atg gag aag cac acc aag gac tac<br>Pro Lys Val Arg Gly Thr Val Leu Met Glu Lys His Thr Lys Asp Tyr<br>            180                 185                 190 | 576 |
| agc gag gtc atc aac gag ccg gtc tct ggc tac tgg agc agc gcc gat<br>Ser Glu Val Ile Asn Glu Pro Val Ser Gly Tyr Trp Ser Ser Ala Asp<br>        195                 200                 205 | 624 |

```
agg agc gcc gct atg ccc ccg gac agc gcc ggt cac ctt ggc ttt gtc      672
Arg Ser Ala Ala Met Pro Pro Asp Ser Ala Gly His Leu Gly Phe Val
    210                 215                 220 tgc atc ttc cac ggc cac gac cac gac acc tgc act ggt ctc ctc acc      720
Cys Ile Phe His Gly His Asp His Asp Thr Cys Thr Gly Leu Leu Thr
225                 230                 235                 240 aag ggc aag gtc aca gat gcc tgc gcc gag ttc acc ttc cac agg gat      768
Lys Gly Lys Val Thr Asp Ala Cys Ala Glu Phe Thr Phe His Arg Asp
                245                 250                 255 taa                                                                  771
```

<210> SEQ ID NO 12
<211> LENGTH: 256
<212> TYPE: PRT
<213> ORGANISM: Arenicola marina

<400> SEQUENCE: 12

```
Met Lys Ser Tyr Val Leu Val Cys Cys Leu Val Val Gly Ala Val Ala
1               5                   10                  15

Tyr Pro His Glu Val Met His His Ala Val Gly Ala Asn Arg Met Cys
            20                  25                  30

Lys Cys Asp Ala Pro Ala Gly Asn Ala Glu Thr Ser Ala Asp Arg Glu
        35                  40                  45

Gln Ser His Thr Leu Asp Glu Leu Thr His Gln Leu His Met Leu Gln
    50                  55                  60

Gln Ala Tyr Asp Thr Gly Met Gly Arg Val Asp Val Met Glu Asp
65                  70                  75                  80

Met Asp Asp Leu Ser His Arg Ile Ala Asp His Glu Lys Glu His Cys
                85                  90                  95

Lys Lys Tyr Arg Glu Phe Gln Cys Gly Gly Asp His Pro Lys Cys Ile
            100                 105                 110

Ser Asn Leu Leu Val Cys Asp Gly Asp Asn Asp Cys Asp Asn Gly Ala
        115                 120                 125

Asp Glu Ala Arg Cys Asp Val Leu Thr Glu Ala Gly Ser Ser Trp Thr
    130                 135                 140

Gly Thr Val Val Tyr Asp His Cys Thr Lys Arg Pro Glu Thr Met
145                 150                 155                 160

Lys Leu Ser Ile Lys Ser Val Asp Thr Val Pro Phe Phe Thr Thr His
                165                 170                 175

Pro Lys Val Arg Gly Thr Val Leu Met Glu Lys His Thr Lys Asp Tyr
            180                 185                 190

Ser Glu Val Ile Asn Glu Pro Val Ser Gly Tyr Trp Ser Ser Ala Asp
        195                 200                 205

Arg Ser Ala Ala Met Pro Pro Asp Ser Ala Gly His Leu Gly Phe Val
    210                 215                 220

Cys Ile Phe His Gly His Asp His Asp Thr Cys Thr Gly Leu Leu Thr
225                 230                 235                 240

Lys Gly Lys Val Thr Asp Ala Cys Ala Glu Phe Thr Phe His Arg Asp
                245                 250                 255
```

<210> SEQ ID NO 13
<211> LENGTH: 376
<212> TYPE: DNA
<213> ORGANISM: Arenicola marina
<220> FEATURE:
<221> NAME/KEY: CDS
<222> LOCATION: (1)..(375)

<223> OTHER INFORMATION:

<400> SEQUENCE: 13

```
gga cct ttg cag cgc ctc ctg gtc aag acc cag tgg aac aag gtg tac      48
Gly Pro Leu Gln Arg Leu Leu Val Lys Thr Gln Trp Asn Lys Val Tyr
1               5                   10                  15 ggc acc agc aag gtc agg gac gag gcc gga cac gtc ctc tgg aag gct      96
Gly Thr Ser Lys Val Arg Asp Glu Ala Gly His Val Leu Trp Lys Ala
            20                  25                  30 att ttc gcc cag gat ccc gag acc cgg gct ctc ttc aag aga gtc aac     144
Ile Phe Ala Gln Asp Pro Glu Thr Arg Ala Leu Phe Lys Arg Val Asn
        35                  40                  45 ggt gac gac atc tac tct ccc gag ttc atg gct cac agc gcc cgt gtc     192
Gly Asp Asp Ile Tyr Ser Pro Glu Phe Met Ala His Ser Ala Arg Val
    50                  55                  60 ttg ggt ggc ctt gac att gcc atc tcc ctc ctc gac aac cag gct gac     240
Leu Gly Gly Leu Asp Ile Ala Ile Ser Leu Leu Asp Asn Gln Ala Asp
65                  70                  75                  80 ctt gac gtc gcc ctg gct cac ctt cac gtg cag cac gta gaa agg cac     288
Leu Asp Val Ala Leu Ala His Leu His Val Gln His Val Glu Arg His
                85                  90                  95 atc cca acc cgc tac ttc gat ctg ttc aag aac gcc ctg atg gag tat     336
Ile Pro Thr Arg Tyr Phe Asp Leu Phe Lys Asn Ala Leu Met Glu Tyr
            100                 105                 110 gcc ccc agc gcc ctg gga cgc tgc ttt gat aag gac gca t               376
Ala Pro Ser Ala Leu Gly Arg Cys Phe Asp Lys Asp Ala
        115                 120                 125
```

<210> SEQ ID NO 14
<211> LENGTH: 125
<212> TYPE: PRT
<213> ORGANISM: Arenicola marina

<400> SEQUENCE: 14

```
Gly Pro Leu Gln Arg Leu Leu Val Lys Thr Gln Trp Asn Lys Val Tyr
1               5                   10                  15

Gly Thr Ser Lys Val Arg Asp Glu Ala Gly His Val Leu Trp Lys Ala
            20                  25                  30

Ile Phe Ala Gln Asp Pro Glu Thr Arg Ala Leu Phe Lys Arg Val Asn
        35                  40                  45

Gly Asp Asp Ile Tyr Ser Pro Glu Phe Met Ala His Ser Ala Arg Val
    50                  55                  60

Leu Gly Gly Leu Asp Ile Ala Ile Ser Leu Leu Asp Asn Gln Ala Asp
65                  70                  75                  80

Leu Asp Val Ala Leu Ala His Leu His Val Gln His Val Glu Arg His
                85                  90                  95

Ile Pro Thr Arg Tyr Phe Asp Leu Phe Lys Asn Ala Leu Met Glu Tyr
            100                 105                 110

Ala Pro Ser Ala Leu Gly Arg Cys Phe Asp Lys Asp Ala
        115                 120                 125
```

<210> SEQ ID NO 15
<211> LENGTH: 288
<212> TYPE: DNA
<213> ORGANISM: Arenicola marina
<220> FEATURE:
<221> NAME/KEY: CDS
<222> LOCATION: (1)..(288)
<223> OTHER INFORMATION:

<400> SEQUENCE: 15

```
tgc gga ccc ctt cag cgc ctg aag gtc aag cgc cag tgg gct gag gct      48
Cys Gly Pro Leu Gln Arg Leu Lys Val Lys Arg Gln Trp Ala Glu Ala
1               5                   10                  15 tat gga agc gga aac agc agg gag gaa ttc gga cac ttc atc tgg tcc      96
Tyr Gly Ser Gly Asn Ser Arg Glu Glu Phe Gly His Phe Ile Trp Ser
            20                  25                  30 cat gtc ttc cag cac tcg cct gct gcc cgc gac atg ttc aag cgc gtc     144
His Val Phe Gln His Ser Pro Ala Ala Arg Asp Met Phe Lys Arg Val
        35                  40                  45 cgc ggt gac aac atc cac acc cca gca ttc atg gcc cac gcc acc cgt     192
Arg Gly Asp Asn Ile His Thr Pro Ala Phe Met Ala His Ala Thr Arg
    50                  55                  60 gtg ctc ggt gga ctc gac atg tgc att gcc ctt ctc gat gat gaa ccc     240
Val Leu Gly Gly Leu Asp Met Cys Ile Ala Leu Leu Asp Asp Glu Pro
65                  70                  75                  80 gtt ctg aac acg cag ctc gct cat ctt gcc aag caa cac gaa acc cgt     288
Val Leu Asn Thr Gln Leu Ala His Leu Ala Lys Gln His Glu Thr Arg
                85                  90                  95

<210> SEQ ID NO 16
<211> LENGTH: 96
<212> TYPE: PRT
<213> ORGANISM: Arenicola marina

<400> SEQUENCE: 16

Cys Gly Pro Leu Gln Arg Leu Lys Val Lys Arg Gln Trp Ala Glu Ala
1               5                   10                  15

Tyr Gly Ser Gly Asn Ser Arg Glu Glu Phe Gly His Phe Ile Trp Ser
            20                  25                  30

His Val Phe Gln His Ser Pro Ala Ala Arg Asp Met Phe Lys Arg Val
        35                  40                  45

Arg Gly Asp Asn Ile His Thr Pro Ala Phe Met Ala His Ala Thr Arg
    50                  55                  60

Val Leu Gly Gly Leu Asp Met Cys Ile Ala Leu Leu Asp Asp Glu Pro
65                  70                  75                  80

Val Leu Asn Thr Gln Leu Ala His Leu Ala Lys Gln His Glu Thr Arg
                85                  90                  95

<210> SEQ ID NO 17
<211> LENGTH: 360
<212> TYPE: DNA
<213> ORGANISM: Arenicola marina
<220> FEATURE:
<221> NAME/KEY: CDS
<222> LOCATION: (1)..(360)
<223> OTHER INFORMATION:

<400> SEQUENCE: 17 aag gtg aag cac caa tgg gtg cag gtg tac agc ggc cat ggt tac gag      48
Lys Val Lys His Gln Trp Val Gln Val Tyr Ser Gly His Gly Tyr Glu
1               5                   10                  15 cgt gag gcg ttc ggc aga gag gtc ttc ctc gag atg tac aac cag gca      96
Arg Glu Ala Phe Gly Arg Glu Val Phe Leu Glu Met Tyr Asn Gln Ala
            20                  25                  30 ccc aag gcc aag gac ctc ttc acc agg gtc agg ggc gag aac gtc ttc     144
Pro Lys Ala Lys Asp Leu Phe Thr Arg Val Arg Gly Glu Asn Val Phe
        35                  40                  45 tcc ccc gag ttc gga gcc cac atg gtc cgt gtg ctc gga ggt ctc gac     192
Ser Pro Glu Phe Gly Ala His Met Val Arg Val Leu Gly Gly Leu Asp
    50                  55                  60
```

```
atg tgc atc gct ctg ctg tcc gat gac acc gtc ctc aac gcc cag ctt    240
Met Cys Ile Ala Leu Leu Ser Asp Asp Thr Val Leu Asn Ala Gln Leu
 65                  70                  75                  80 gct cac ctc agc acg cag cac aag gac cgt gga atc ccc aac gag tac    288
Ala His Leu Ser Thr Gln His Lys Asp Arg Gly Ile Pro Asn Glu Tyr
                 85                  90                  95 ttc gat gtg gtg aag gtc gcc ctc atg aag gtc gtc ccc ggc cac gtt    336
Phe Asp Val Val Lys Val Ala Leu Met Lys Val Val Pro Gly His Val
            100                 105                 110 tca cac ttc gat atc ggc gcg tgg                                    360
Ser His Phe Asp Ile Gly Ala Trp
        115                 120

<210> SEQ ID NO 18
<211> LENGTH: 120
<212> TYPE: PRT
<213> ORGANISM: Arenicola marina

<400> SEQUENCE: 18

Lys Val Lys His Gln Trp Val Gln Val Tyr Ser Gly His Gly Tyr Glu
 1               5                  10                  15

Arg Glu Ala Phe Gly Arg Glu Val Phe Leu Glu Met Tyr Asn Gln Ala
             20                  25                  30

Pro Lys Ala Lys Asp Leu Phe Thr Arg Val Arg Gly Glu Asn Val Phe
         35                  40                  45

Ser Pro Glu Phe Gly Ala His Met Val Arg Val Leu Gly Gly Leu Asp
     50                  55                  60

Met Cys Ile Ala Leu Leu Ser Asp Asp Thr Val Leu Asn Ala Gln Leu
 65                  70                  75                  80

Ala His Leu Ser Thr Gln His Lys Asp Arg Gly Ile Pro Asn Glu Tyr
                 85                  90                  95

Phe Asp Val Val Lys Val Ala Leu Met Lys Val Val Pro Gly His Val
            100                 105                 110

Ser His Phe Asp Ile Gly Ala Trp
        115                 120

<210> SEQ ID NO 19
<211> LENGTH: 390
<212> TYPE: DNA
<213> ORGANISM: Arenicola marina
<220> FEATURE:
<221> NAME/KEY: CDS
<222> LOCATION: (1)..(390)
<223> OTHER INFORMATION:

<400> SEQUENCE: 19 tgt tgc agt ata gag gac cgc aag gag gtc cag acg ctg tgg agt gag    48
Cys Cys Ser Ile Glu Asp Arg Lys Glu Val Gln Thr Leu Trp Ser Glu
 1               5                  10                  15 atc tgg agt gcc cag ttc act ggt cgc cgt gtc cag gtt gcc cag gct    96
Ile Trp Ser Ala Gln Phe Thr Gly Arg Arg Val Gln Val Ala Gln Ala
             20                  25                  30 gtg ttc gag gac ctc ttc cgc cgc gac ccc gag tcc aag aac ctg ttc    144
Val Phe Glu Asp Leu Phe Arg Arg Asp Pro Glu Ser Lys Asn Leu Phe
         35                  40                  45 aag cgc gtc aat gtt gac gac atg aac agc ccc gaa ttc cac gct cac    192
Lys Arg Val Asn Val Asp Asp Met Asn Ser Pro Glu Phe His Ala His
     50                  55                  60 tgc atc cgt gtt gtc aac ggt ctt gac acc gtg atc ggt ctc ctt gac    240
Cys Ile Arg Val Val Asn Gly Leu Asp Thr Val Ile Gly Leu Leu Asp
 65                  70                  75                  80
```

```
gac ccc gac acc ctg aag tcc cag ctc gag cac ttg gcc cag cag cac      288
Asp Pro Asp Thr Leu Lys Ser Gln Leu Glu His Leu Ala Gln Gln His
                85                  90                  95 aag gag cgt gat ggc atc cac aag acc cac ttc gac gag atg tcc cac      336
Lys Glu Arg Asp Gly Ile His Lys Thr His Phe Asp Glu Met Ser His
            100                 105                 110 gcc ttc ggc gcc gtc atg ccc cag gtc agc agc tgt ttc aac ccc gat      384
Ala Phe Gly Ala Val Met Pro Gln Val Ser Ser Cys Phe Asn Pro Asp
        115                 120                 125 gca tga                                                              390
Ala

<210> SEQ ID NO 20
<211> LENGTH: 129
<212> TYPE: PRT
<213> ORGANISM: Arenicola marina

<400> SEQUENCE: 20

Cys Cys Ser Ile Glu Asp Arg Lys Glu Val Gln Thr Leu Trp Ser Glu
1               5                   10                  15

Ile Trp Ser Ala Gln Phe Thr Gly Arg Arg Val Gln Val Ala Gln Ala
            20                  25                  30

Val Phe Glu Asp Leu Phe Arg Arg Asp Pro Glu Ser Lys Asn Leu Phe
        35                  40                  45

Lys Arg Val Asn Val Asp Asp Met Asn Ser Pro Glu Phe His Ala His
    50                  55                  60

Cys Ile Arg Val Val Asn Gly Leu Asp Thr Val Ile Gly Leu Leu Asp
65                  70                  75                  80

Asp Pro Asp Thr Leu Lys Ser Gln Leu Glu His Leu Ala Gln Gln His
                85                  90                  95

Lys Glu Arg Asp Gly Ile His Lys Thr His Phe Asp Glu Met Ser His
            100                 105                 110

Ala Phe Gly Ala Val Met Pro Gln Val Ser Ser Cys Phe Asn Pro Asp
        115                 120                 125

Ala

<210> SEQ ID NO 21
<211> LENGTH: 20
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (9)..(9)
<223> OTHER INFORMATION: A, G, C or T
<220> FEATURE:
<221> NAME/KEY: misc_feature
<222> LOCATION: (12)..(12)
<223> OTHER INFORMATION: A, G, C or T

<400> SEQUENCE: 21
gartgyggnc cnttrcarcg                                                 20

<210> SEQ ID NO 22
<211> LENGTH: 21
<212> TYPE: DNA
<213> ORGANISM: artificial sequence
<220> FEATURE:
<223> OTHER INFORMATION: PCR primer

<400> SEQUENCE: 22
```

```
ctcctctcct ctcctcttcc t                                           21

<210> SEQ ID NO 23
<211> LENGTH: 17
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (6)..(6)
<223> OTHER INFORMATION: A, G, C or T
<220> FEATURE:
<221> NAME/KEY: misc_feature
<222> LOCATION: (12)..(12)
<223> OTHER INFORMATION: A, G, C or T

<400> SEQUENCE: 23
tgyggnathc tncarcg                                                17

<210> SEQ ID NO 24
<211> LENGTH: 18
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (6)..(6)
<223> OTHER INFORMATION: inosine
<220> FEATURE:
<221> NAME/KEY: misc_feature
<222> LOCATION: (12)..(12)
<223> OTHER INFORMATION: A, G, C or T

<400> SEQUENCE: 24
aargtnaarc anaactgg                                               18

<210> SEQ ID NO 25
<211> LENGTH: 20
<212> TYPE: DNA
<213> ORGANISM: artificial sequence
<220> FEATURE:
<223> OTHER INFORMATION: PCR primer

<400> SEQUENCE: 25
tgytgyagya thgargaycg                                             20

<210> SEQ ID NO 26
<211> LENGTH: 20
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (6)..(6)
<223> OTHER INFORMATION: A, G, C or T
<220> FEATURE:
<221> NAME/KEY: misc_feature
<222> LOCATION: (15)..(15)
<223> OTHER INFORMATION: A, G, C or T

<400> SEQUENCE: 26
aargtnatht tyggnagrga                                             20

<210> SEQ ID NO 27
<211> LENGTH: 20
<212> TYPE: DNA
```

```
<213> ORGANISM: artificial sequence
<220> FEATURE:
<223> OTHER INFORMATION: PCR primer
<220> FEATURE:
<221> NAME/KEY: misc_feature
<222> LOCATION: (15)..(15)
<223> OTHER INFORMATION: A, G, C or T
<220> FEATURE:
<221> NAME/KEY: misc_feature
<222> LOCATION: (18)..(18)
<223> OTHER INFORMATION: A, G, C or T

<400> SEQUENCE: 27
garcaycart gyggnggnga                                         20

<210> SEQ ID NO 28
<211> LENGTH: 21
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (4)..(4)
<223> OTHER INFORMATION: A, G, C or T
<220> FEATURE:
<221> NAME/KEY: misc_feature
<222> LOCATION: (7)..(7)
<223> OTHER INFORMATION: A, G, C or T

<400> SEQUENCE: 28
ccangcntcy ttrtcraagc a                                       21

<210> SEQ ID NO 29
<211> LENGTH: 19
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (2)..(2)
<223> OTHER INFORMATION: A, G, C or T
<220> FEATURE:
<221> NAME/KEY: misc_feature
<222> LOCATION: (8)..(8)
<223> OTHER INFORMATION: A, G, C or T
<220> FEATURE:
<221> NAME/KEY: misc_feature
<222> LOCATION: (11)..(11)
<223> OTHER INFORMATION: A, G, C or T
<220> FEATURE:
<221> NAME/KEY: misc_feature
<222> LOCATION: (14)..(14)
<223> OTHER INFORMATION: A, G, C or T

<400> SEQUENCE: 29
antgyggncc nctncarcg                                          19

<210> SEQ ID NO 30
<211> LENGTH: 18
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (4)..(4)
<223> OTHER INFORMATION: A, G, C or T
<220> FEATURE:
<221> NAME/KEY: misc_feature
<222> LOCATION: (7)..(7)
<223> OTHER INFORMATION: A, G, C or T
```

```
<400> SEQUENCE: 30
ccangcnccd atrtcraa                                          18

<210> SEQ ID NO 31
<211> LENGTH: 20
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (3)..(3)
<223> OTHER INFORMATION: A, G, C or T
<220> FEATURE:
<221> NAME/KEY: misc_feature
<222> LOCATION: (6)..(6)
<223> OTHER INFORMATION: A, G, C or T

<400> SEQUENCE: 31
cangcnycrc trttraarca                                        20
```